(12) United States Patent
Ruth et al.

(10) Patent No.: US 11,844,663 B2
(45) Date of Patent: Dec. 19, 2023

(54) LIGHT CURING DENTAL SYSTEM

(71) Applicant: DENTSPLY SIRONA Inc., York, PA (US)

(72) Inventors: Thomas Ruth, South Easton, MA (US); William Kane, Sutton, MA (US); Joseph Gordon, Mansfield, MA (US); Luke Hagan, Seattle, WA (US); David Copeland, Minnetonka, MN (US); Andrew Burke, Saunderstown, RI (US); Dustin Gaidos, Milton, MA (US); Christos Angeletakis, Bear, DE (US)

(73) Assignee: DENTSPLY SIRONA INC., York, PA (US)

( * ) Notice: Subject to any disclaimer, the term of this patent is extended or adjusted under 35 U.S.C. 154(b) by 127 days.

(21) Appl. No.: 17/476,559

(22) Filed: Sep. 16, 2021

(65) Prior Publication Data

US 2022/0000590 A1    Jan. 6, 2022

Related U.S. Application Data

(63) Continuation of application No. 15/880,222, filed on Jan. 25, 2018, now abandoned.

(51) Int. Cl.
| | | |
|---|---|---|
| *A61C 9/00* | (2006.01) | |
| *A61C 13/15* | (2006.01) | |
| *A61C 19/06* | (2006.01) | |
| *A61C 7/14* | (2006.01) | |
| *A61C 7/02* | (2006.01) | |
| *A61N 5/06* | (2006.01) | |
| *A61C 1/08* | (2006.01) | |
| *A61C 13/00* | (2006.01) | |

(52) U.S. Cl.
CPC ............ *A61C 9/0006* (2013.01); *A61C 7/023* (2013.01); *A61C 7/146* (2013.01); *A61C 9/0013* (2013.01); *A61C 19/003* (2013.01); *A61C 19/004* (2013.01); *A61C 19/066* (2013.01); *A61N 5/0603* (2013.01); *A61C 1/088* (2013.01); *A61C 13/0027* (2013.01); *A61C 19/06* (2013.01); *A61C 19/063* (2013.01); *A61C 2204/002* (2013.01); *A61N 5/0613* (2013.01); *A61N 2005/0653* (2013.01)

(58) Field of Classification Search
CPC ... A61C 9/0006; A61C 9/0013; A61C 19/066; A61C 19/003; A61C 19/004; A61C 19/06; A61C 19/063; A61C 7/146; A61C 7/023; A61C 2204/002; A61N 5/0603; A61N 5/0613; A61N 2005/0653
USPC ............................................................ 433/29
See application file for complete search history.

(56) References Cited

U.S. PATENT DOCUMENTS 4,553,936 A  * 11/1985  Wang .................... A61C 9/0006
                                                       433/229
5,316,473 A  *  5/1994  Hare .................... A61C 19/004
                                                         433/29

(Continued)

*Primary Examiner* — Matthew M Nelson
(74) *Attorney, Agent, or Firm* — DENTSPLY SIRONA INC.

(57) ABSTRACT

A light curing dental system comprising a light emitting tray that precisely distributes an optimal amount of curing light energy to internal, external and extra oral portions of the dental arch to cure a dental material. The light curing dental system generally includes a light source, a light emitting dental tray, an activation module and a photocurable dental material.

19 Claims, 33 Drawing Sheets

(56) References Cited

U.S. PATENT DOCUMENTS

| | | | | |
|---|---|---|---|---|
| 5,487,662 | A * | 1/1996 | Kipke | A61C 9/0006 |
| | | | | 433/29 |
| 6,077,073 | A * | 6/2000 | Jacob | A61C 19/066 |
| | | | | 433/29 |
| 7,144,249 | B2 * | 12/2006 | Rizoiu | A61N 5/0603 |
| | | | | 433/29 |
| 8,620,451 | B2 * | 12/2013 | Kennedy | A61N 5/0616 |
| | | | | 607/101 |
| 9,066,777 | B2 * | 6/2015 | Gill | F21V 19/02 |
| 9,084,587 | B2 * | 7/2015 | Eckhouse | A61B 18/203 |
| 9,730,780 | B2 * | 8/2017 | Brawn | A61C 19/006 |
| 9,974,630 | B2 * | 5/2018 | Heacock | A61C 1/0046 |
| 2012/0064477 | A1 * | 3/2012 | Schmitt | A61B 5/0022 |
| | | | | 433/44 |
| 2013/0052607 | A1 * | 2/2013 | Gersh | A61C 19/004 |
| | | | | 433/27 |

\* cited by examiner

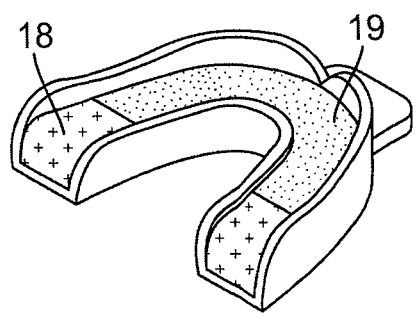
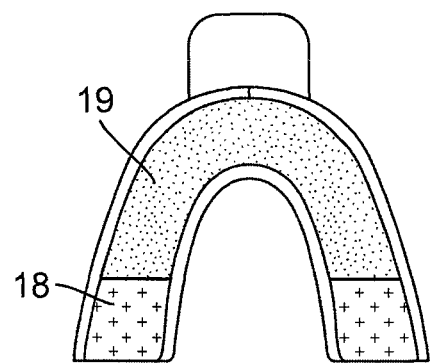
FIG. 9a  FIG. 9b
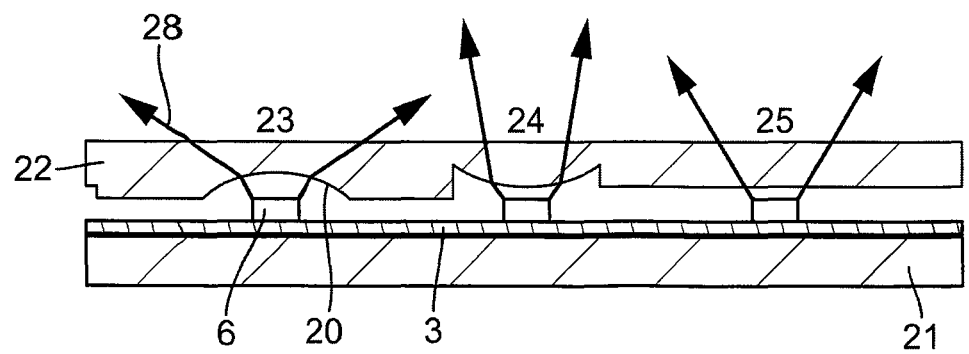
FIG. 10

 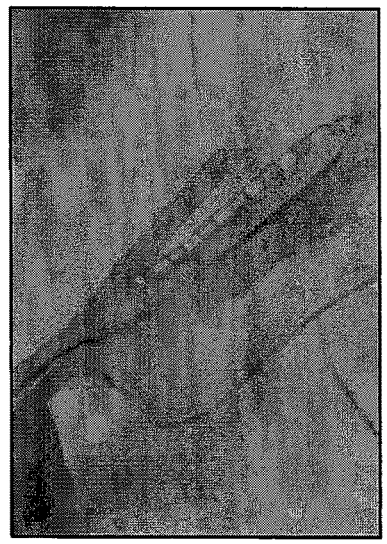 
FIG. 26a  FIG. 26b  FIG. 26c

LIGHT CURING DENTAL SYSTEM

This application is a continuation of U.S. application Ser. No. 15/880,222, filed Jan. 25, 2018, which claims priority to U.S. Provisional Application No. 62/450,211 filed Jan. 25, 2017.

BACKGROUND

The present disclosure relates generally to a light curing impression system and more specifically to a dental impression light curing system comprising a light emitting tray that precisely distributes light from light emitting sources and provides control over the amount of light energy to internal, external and extra oral portions of the oral cavity and dental anatomy to allow for the efficient and rapid curing of impression material.

Light curing impressions have not been commercially successful in the past for many reasons. Light curing of impression materials using a conventional curing lamp takes a long time. Also, prior illumination trays were shown to not be able to cure all the impression material in the mouth because light was not able to reach all the regions in the mouth or external areas of the tray.

Many light sources and trays are known in the art to be used to cure impression material. The light is delivered over a range of wavelengths. Some of light sources include LEDs and Lasers. U.S. Pat. No. 6,514,075 discloses an elastomeric wand with embedded LEDs and an aseptic barrier sleeve for curing dental adhesives or activating whitening agents.

U.S. Patent Application Publication No. 2008/0038685 provides an electroluminescent strip for low heat generation and uniform irradiation of the dental arch. Such strips have low intensity and illuminate only in one direction and are therefore not be able to cure material in overflow areas outside of impression tray boundaries.

U.S. Pat. No. 5,316,473 discloses a U-shaped curing light probe illuminated with fiber optic bundles or LEDs, prefilled tray inserts that fit within Illuminated LED or fiber optic trays and a double arch tray with a removable mesh component for removing the impression and reusing the tray. However, the device cannot easily cure material that inevitably overflows the boarders of the tray. The light source also incorporates a plurality of fiber optic filaments making the device bulky and expensive to manufacture. U.S. Pat. No. 5,487,662 discloses a dental impression tray including a self-contained light source for curing photo curable impression material. However this device lacks the ability to cure overflow material. U.S. Pat. No. 5,702,250 discloses a double arch tray with a an array of LED lights on the buccal and lingual walls of said tray and a slide-able mesh insert that can be removed from the tray. However the device is bulky with a battery housed in a pocket adjacent to the buccal sidewall of the tray. Dental impression trays with chemiluminescent light sources also exist in the art, an example of which is U.S. Pat. No. 5,718,577. The tray which comprises a body having wall portions defining at least one channel for receiving a quantity of photo curable dental impression material, also includes a chamber for receiving a chemiluminescent composition and an inlet opening in communication with the chamber for admitting chemiluminescent composition into the chamber. The tray enables the chemiluminescent light source to be in close proximity to the dental impression material and enables the emitted light to be distributed to various regions of the dental impression material for curing. Actinic light rays are used in prior art to effect polymerization of impression material and are disclosed for example in U.S. Pat. No. 4,867,682. U.S. Pat. No. 6,077,073 discloses a sheathed, multi-tooth light emitting diode-array light apparatus for curing adhesives, sealants and/or whitening or coloring agents. The device has a housing and an LED array contained within the housing so as to be maintained in non-contacting relation with the human mouth. The device is however best used with adhesives, sealants and whitening/coloring agents and is not ideal for use with impression materials as separate impression trays will make the device bulky for insertion in the mouth. U.S. Pat. No. 7,144,249 teaches a device for exposing teeth to electromagnetic radiation for whitening and hygiene. However it is not directed to the curing of impression material. Other trays exist in the prior art that are directed to dental treatment applications such as teeth whitening, teeth desensitization and periodontal disease prevention and are disclosed in U.S. Pat. Nos. 8,215,954, 8,371,853 and U.S. Patent Application Publication No. 2015/0079536 A1.

The volumes of material found to be difficult to cure when using an illumination tray include: material flowing toward the distal soft palate, material going below the tongue in the posterior area, the thick material flowing in deep hard palate, material in the interproximal area or in areas of shadows created by more opaque restorations and material in the vestibules. Making an illumination tray able to cure all impression material volume poses multiple challenges in terms of correct light orientation, heat management, adaptation to different types and size of trays (e.g. full arch, segmented, triple trays), making the system ergonomic and easy to use and finally bringing the system to a reasonable cost per use for the user while enabling adequate control of cross contamination.

SUMMARY

It is desirable in many uses to provide a cheaper, easy to use and less bulky system which can cure overflowing impression material through the precise direction of curing light to areas of the tray and outside the tray that traditionally do not get enough curing light. It is also desirable to provide a tray that can be reused or disinfected as well as a single use, disposable trays. A tray with a removable electronics module that can be separated from the reusable tray so that the electronics do not get subjected to the harsh environment of autoclaving is desired. Furthermore, a tray that is hermetically sealed to prohibit the ingress of steam from the autoclaving process is desired. The tray may only contain LEDs or light sources which can tolerate the autoclaving heat. A tray with a small rechargeable battery to power a curing light activation module is also desired.

The light curing impression tray system described hereinafter can reduce the time it takes to record an impression to under 30 seconds. This is not only beneficial to the practitioner but to the patient as well, because the material is in the mouth for a shorter period of time. For example, common fast set impression materials typically require 2.5 minutes of curing in the mouth. Regular set materials can typically take 5 minutes or longer. During this time patients often gag on the material causing them discomfort and uncontrolled mouth movements when the material is setting and resulting in impression defects.

Existing limitations associated with the foregoing, as well as other limitations, can be overcome by the disclosure which generally relates to an impression system comprising a light source, an impression tray, an activation/rechargeable module and impression material.

There has thus been outlined, rather broadly, some of the features of the disclosure in order that the detailed description thereof may be better understood, and in order that the present contribution to the art may be better appreciated. There are additional features of the disclosure that will be described hereinafter.

In this respect, before explaining at least one embodiment of the disclosure in detail, it is to be understood that the disclosure is not limited in its application to the details of construction or to the arrangements of the components set forth in the following description or illustrated in the drawings. The disclosure is capable of other embodiments and of being practiced and carried out in various ways. Also, it is to be understood that the phraseology and terminology employed herein are for the purpose of the description and should not be regarded as limiting.

Curing lights are hereinafter collectively referred to as light or curing light or the like and the trays are hereinafter collectively referred to as light curing trays, dental impression trays, trays, light curing impression systems, dental impression light curing system or the like.

One object is to provide a dental impression light curing system comprised of a light emitting tray that precisely distributes light from light emitting sources and provides control over the amount of light energy to internal, external and extra oral portions of the oral cavity and dental anatomy to allow for the efficient and rapid curing of impression material.

Another object is to provide a light curing impression system that that precisely delivers an optimal amount of energy to internal, external and extra oral portions of the system to enable light curing of impression material and to limit the amount of heat generated.

Yet another object is to provide a light curing impression system that makes a dental impression more easily and more quickly than other impression systems including digital impression systems. This system is easier because a hydrophilic wash material can be easily and precisely placed around the tooth preparation and can then be cured at will with a light emitting tray in a few seconds.

Another object is to provide a light curing impression system comprising pre-filled impression material 110 trays including single and double arch impression trays. It also relates to a method of making the pre-filled impression system.

Another object is to provide a light curing impression system that cures impression material using an LED (Light-Emitting Diode) or OLED (Organic-Light Emitting Diode) light source.

Another object is to provide a light curing impression system that cures impression material using a light source wherein the light source is delivered by a light pipe coupled to an illumination source such as an LED or a Laser. This will have the advantage of having the heat generated by the illumination means being generated outside the mouth and result in a lower cost disposable tray only made in plastic: Plastic tray and plastic light pipe. In addition, the light pipe may incorporate notches to extract the light at desired areas of the tray. The size and placement of the notches can be adjusted to vary the intensity of light escaping and thereby optimizing performance.

Another object is to provide a light curing impression system that cures impression material using a chip on board (COB) LED light source.

Another object is to provide a light curing impression system that cures impression material using a laser light source.

Another object is to provide a light curing impression system that cures impression material using a light source wherein the light source is a flexible LED strip.

Another object is to provide a light curing impression system that cures impression material using a light source wherein the light source is pulsed with high intensity peaks to get deeper penetration of curing material and less heat generation.

Another object is to provide a light curing impression system that is designed to minimize the total thickness of impression material distributed over the light sources and accordingly reduce the energy needed and the heat generated by the light sources in the patient's mouth.

Another object is to provide a light curing impression system that is autoclavable with all its electronic components, if any, (e.g. LEDs, resistors, ICs, etc. can all be autoclaved when appropriately sealed).

Another object is to provide a light curing impression system that has electronics for providing power and activation to the light source and wherein the power and activation circuits are operably removable from the tray and are housed in an energy attachment unit.

Other objects and advantages described herein will become obvious to the reader and it is intended that these objects and advantages are within the scope of the present disclosure. To the accomplishment of the above and related objects, this disclosure may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present disclosure will become fully appreciated as the same becomes better understood when considered in conjunction with the accompanying drawings, in which like reference characters designate the same or similar parts throughout the several views, and wherein:

FIG. 9a shows an isometric view of a LED light tray with a prefilled putty viscosity in the posterior section of the tray forming a thick dam to minimize the amount of material that can squeeze out into the throat or soft palate.

FIG. 9b shows a top view of the tray of FIG. 9a.

FIG. 10 shows a cross section of an LED impression tray where lenses over the individual LED's either disperses or focuses the light for adjusting the light intensity and dispersion.

FIG. 24 b shows a second stage of insertion of the strip of FIG. 23 into a channel as could be made in a triple tray.

FIG. 24 c shows a third stage of insertion of the strip of FIG. 23 into a channel as could be made in a triple tray.

FIG. 24 d shows a fourth stage of insertion of the strip of FIG. 23 into a channel as could be made in a triple tray.

FIG. 25 b shows a second stage of insertion of the strip of FIG. 23 into 2 channels as could be made in a full arch tray.

FIG. 25 c shows a third stage of insertion of the strip of FIG. 23 into 2 channels as could be made in a full arch tray.

FIG. 25 d shows a fourth stage of insertion of the strip of FIG. 23 into 2 channels as could be made in a full arch tray.

FIG. 26 a shows a top view of a channel as in FIG. 24 in a tray prototype for illumination.

FIG. 26 b shows a side view of a channel as in FIG. 24 in a tray prototype for illumination.

FIG. 26 c shows a top view of a channel as in FIG. 24 in a tray prototype for illumination with the strip powered on.

FIG. 29 shows the coupling mechanism of the light pipe triple tray of FIG. 30b.

FIG. 37 shows another embodiment of the triple tray of FIG. 36.

FIG. 38 shows an illustration of a small lightweight, remote power source for the COB/PCB light tray. Such power source being clipped to the patient bib, bib chain, safety glasses or hand held.

FIG. 39 shows an illustration of a light pipe illumination tray with a remote power source and the light engine and heat sink adjacent to the tray for optimal light transmission, while reducing weight at the mouth which could impinge on impression quality.

FIG. 40 shows a diagram of a triple tray light pipe illuminated tray with a reflective coating on the outside to reflect light towards the dentition and selective clear areas on the upper and lower edges of the sidewalls that permit light to escape and cure material that overflows the tray borders.

DETAILED DESCRIPTION

Figure 1:
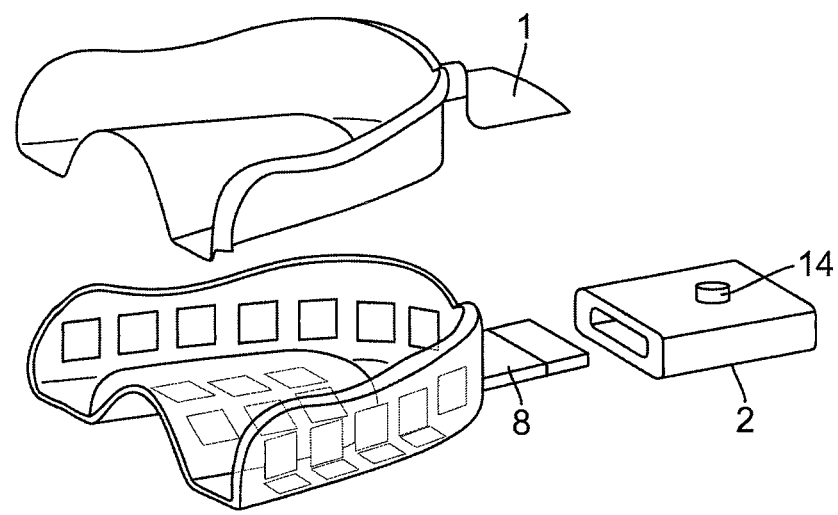
FIG. 1 is an exploded upper perspective view of an embodiment of the present disclosure. It illustrates a reusable LED tray with a prefilled impression tray insert (impression material not shown) and a rechargeable activation module.

Turning now descriptively to the drawings, in which similar reference characters denote similar elements throughout the several views, the figures illustrate a light transmission, an impression tray, an activation module and impression material. In some cases, the impression material is not shown in illustrations of pre-filled trays for clarity.

Figure 4A:
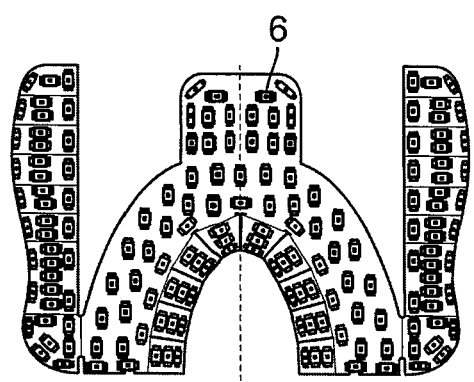
FIG. 4a is a plan view of a flexible PCB showing the placement of three types of LEDs; top, side and bottom emitting.
Figure 4B:
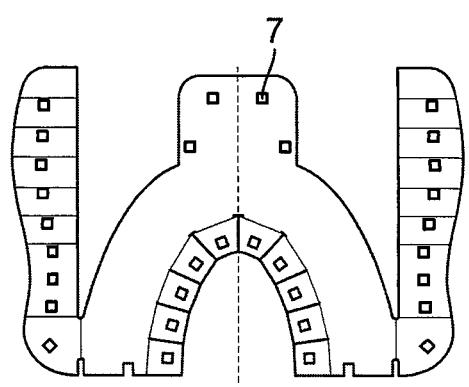
FIG. 4b is a plan view of the Flexible PCB of FIG. 4a without the LEDs, showing the square holes for bottom emitting LEDs to illuminate the reverse side of the Flexible circuit and the outside of the tray. The fine lines represent the fold lines.

FIG. 1-FIG. 13 are diagrams illustrating various components of a reusable LED tray 8 in accordance with embodiments of the disclosure. A prefilled impression tray insert 1 (impression material not shown) sits on top of a reusable LED tray 8 and a rechargeable activation module 2 connects to the tray 8 to supply power to the tray 8. The embodiment comprises light emitting diodes (LEDs) 6 (as shown in FIG. 4) embedded in an impression tray 8 to cure a light curable dental impression material (not shown). The tray can be an open bite tray 8 (a.k.a. single arch tray) or a closed bite tray 8a, FIG. 6 (a.k.a. double arch tray or triple tray). The LEDs 6 are hermetically sealed in a plastic housing 4, 5 that is shaped like the desired impression tray. The LEDs 6 and circuit wiring (not shown) are capable of tolerating high temperatures. Being hermetically sealed, the circuit is protected from moisture and therefore the tray 8 is able to be sterilized between patients.

The wavelength of the light 28 emitted from the LEDs 6 may be in the visible blue light range from 450 to 490 nm and may be 465 nm in order to match the photo initiator camphorquinone (CQ). However the device has utility for curing materials with other photoinitiators at different wavelengths, for example from 380 to 700 nm.

Figure 2:
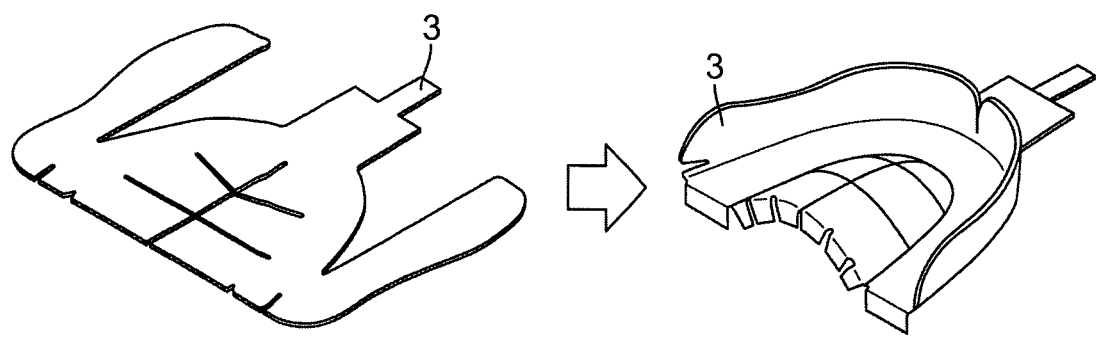
FIG. 2 is an upper perspective view of an embodiment. It illustrates a flexible printed circuit board (PCB) substrate (LEDs not shown) and how the substrate would be folded into a configuration suitable for encapsulation in plastic to form a reusable LED tray. This embodiment of the Flexible PCB has panels that fold toward the throat and soft palate of the patient's mouth to cure the overflow areas of the tray.
Figure 3:
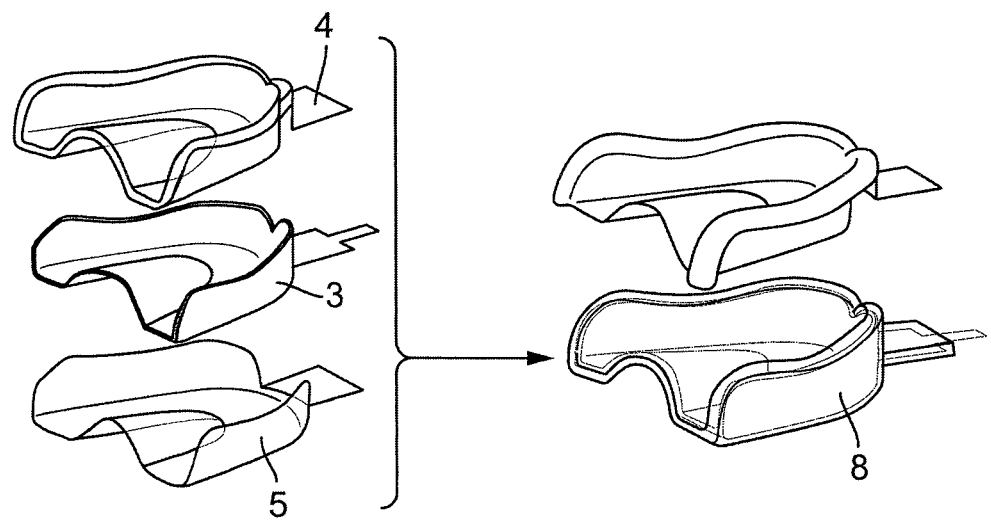
FIG. 3 is an upper perspective view of an embodiment. On the left is an illustration of the flexible PCB encapsulation between two halves of an impression tray form and further showing how the assembly forms the lower LED tray of the illustration on the right.
Figure 15:
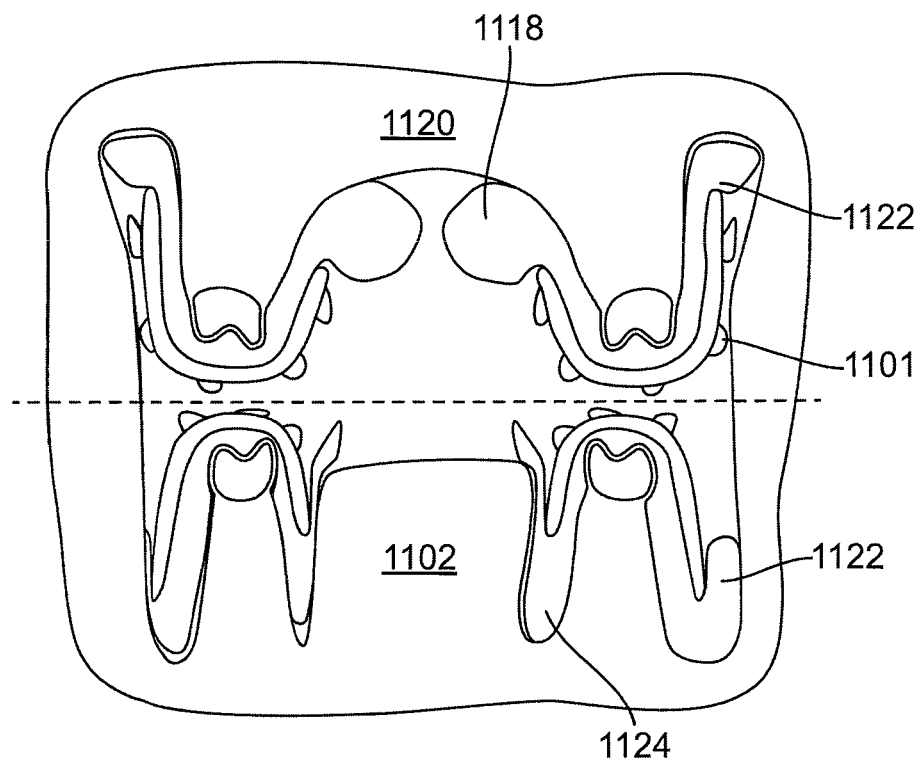
FIG. 15 is a cross section diagram of the dental anatomy and single arch impression trays indicating the hard palate, vestibules and lingual posterior areas that are prone to overflow and hard to cure.
Figure 16:
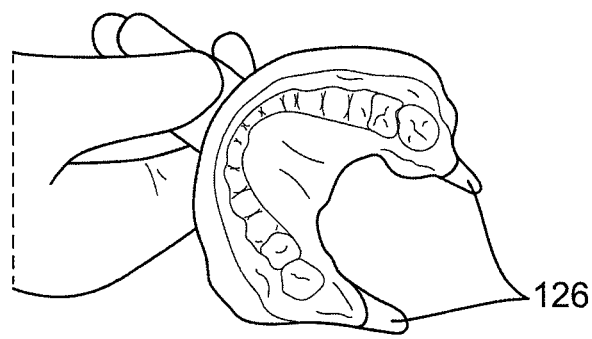
FIG. 16 is shows an impression showing the lingual posterior areas that are hard to cure.
Figure 17:
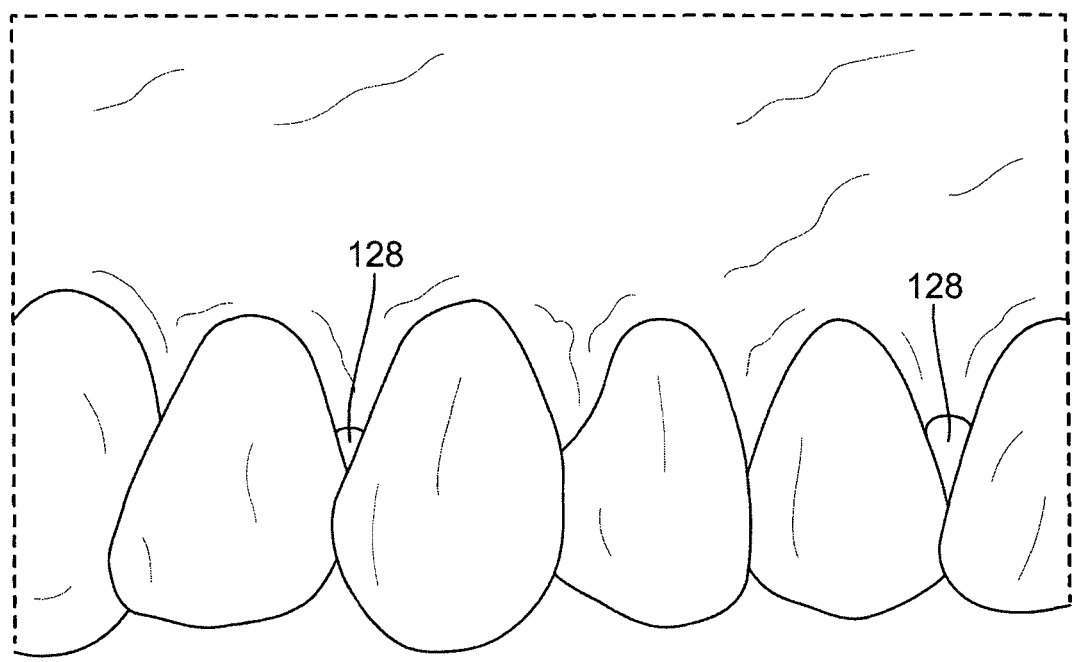
FIG. 17 illustrates large interproximal areas that are hard to cure.
Figure 18:
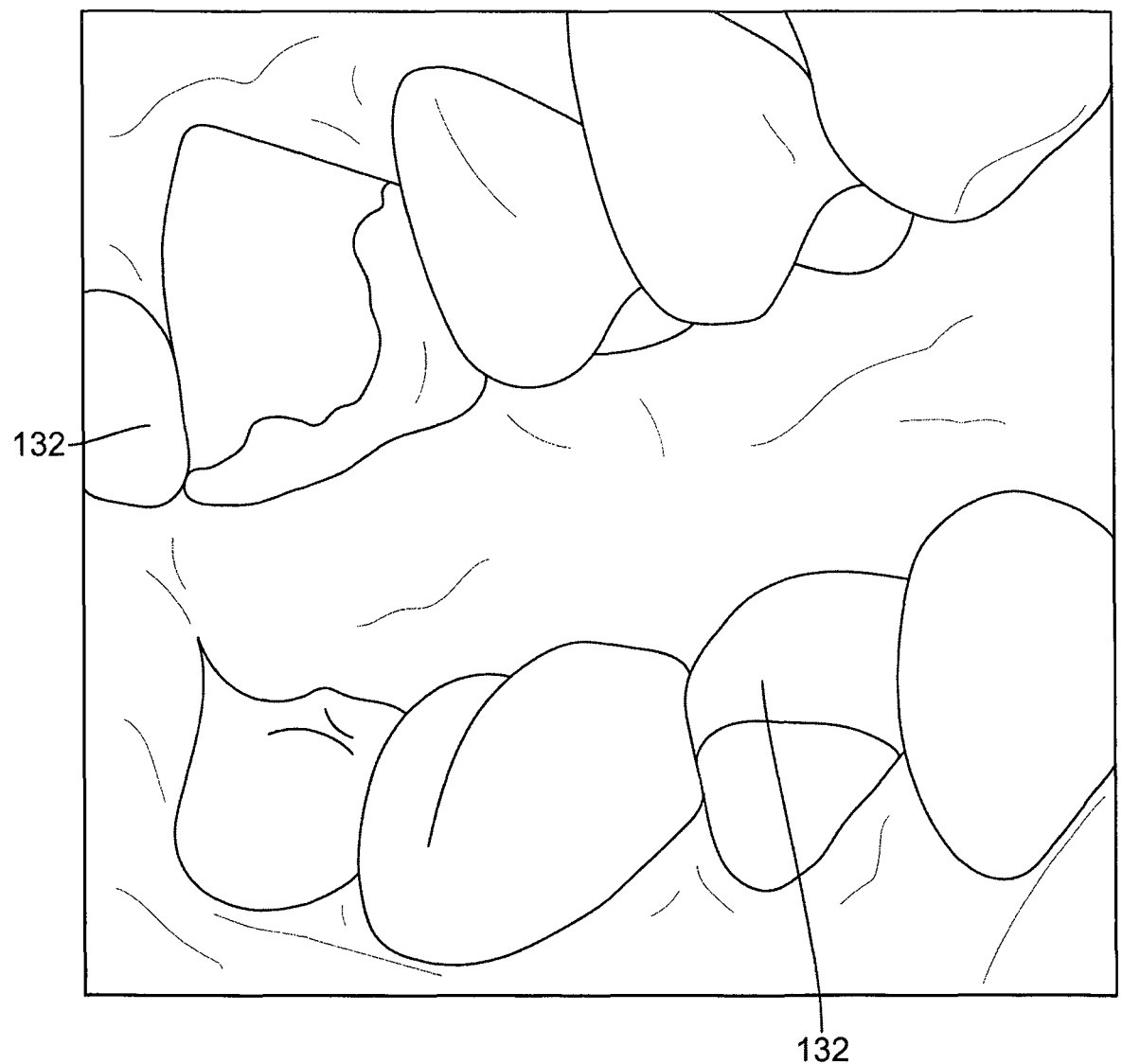
FIG. 18 shows metal restorations that are opaque and would cast shadows and areas that are hard to cure.
Figure 19:
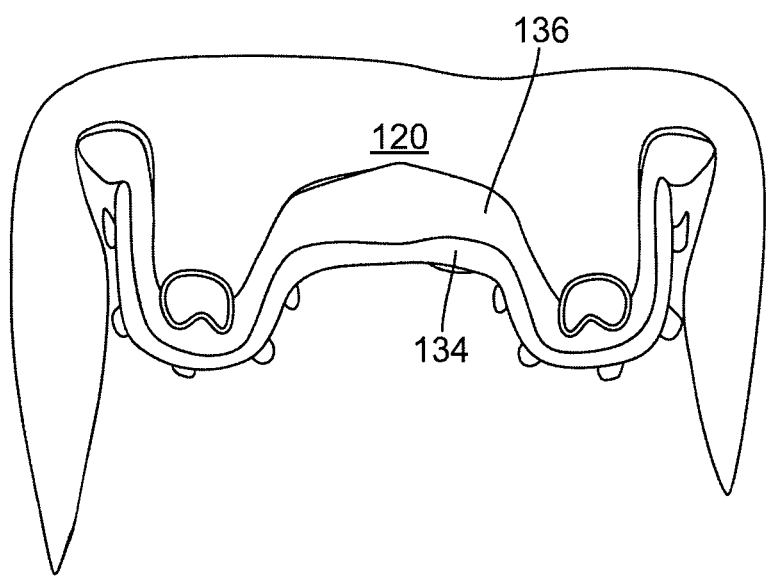
FIG. 19 is an illustration of an upper tray with a palatal area and the resulting thick area of impression material that must be cured.
Figure 20:
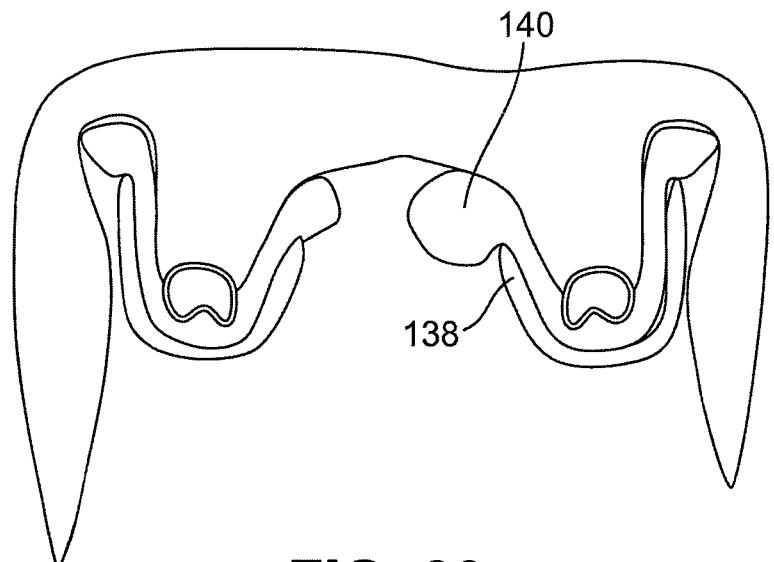
FIG. 20 is an illustration of an upper tray without a palatal area and the resulting overflow which must be cured.

The LEDs 6 may be mounted on a flexible printed circuit board (PCB) 3 that permits the LED circuit (not shown) to be bent into a configuration conforming to the shape of a dental impression tray (FIG. 2). Most of the LEDs are oriented towards the dental arch in order to cure the dental impression material surrounding the teeth. Some LEDs 6 may be oriented to emit light 28b, FIG. 22 towards the outside edges of the LED impression tray 8 in order to cure impression material that invariably overflows 118, 122,124, FIG. 15 the boundaries of the tray, the outside surfaces of the tray and the soft palate area of the mouth where overflow can accumulate outside of the tray. For example, as shown in FIG. 4a the LEDs 6 oriented towards the teeth can be top-emitting LEDs, the LEDs oriented to the outside of the tray can be bottom-emitting LEDs and LEDs orienting to the edge of the vertical edges of the tray can be side-emitting LEDs.

In accordance with another embodiment, the device 8 may be powered by a rechargeable battery with DC current (FIG. 1, Activation Module 2). In alternative embodiments, the battery may be attached to a PCB that also includes a programmable integrated circuit chip that is preprogramed with the curing sequence and circuit detection program (not shown) that detects whether the LEDs (or other curing light source) and battery are ready for activation (i.e. a go/no-go circuit). The PCB may also contain an activation button 14 and an LED light 65 that indicates go/no-go based on the circuit and battery status. The battery and PCB comprise an activation module 2 that can connect to the LED curing tray 8. The activation module 2 may be detached and the surface disinfected separately from the tray 8 so that it does not have to be subjected to sterilization, which would be detrimental to the electronics. The activation modules 2 may be paired with specific trays depending on the number of LEDs 6 etc. or a single activation module can be programmed to auto detect the type of tray it is connected to and impart the correct charging sequence as required.

Figure 38:
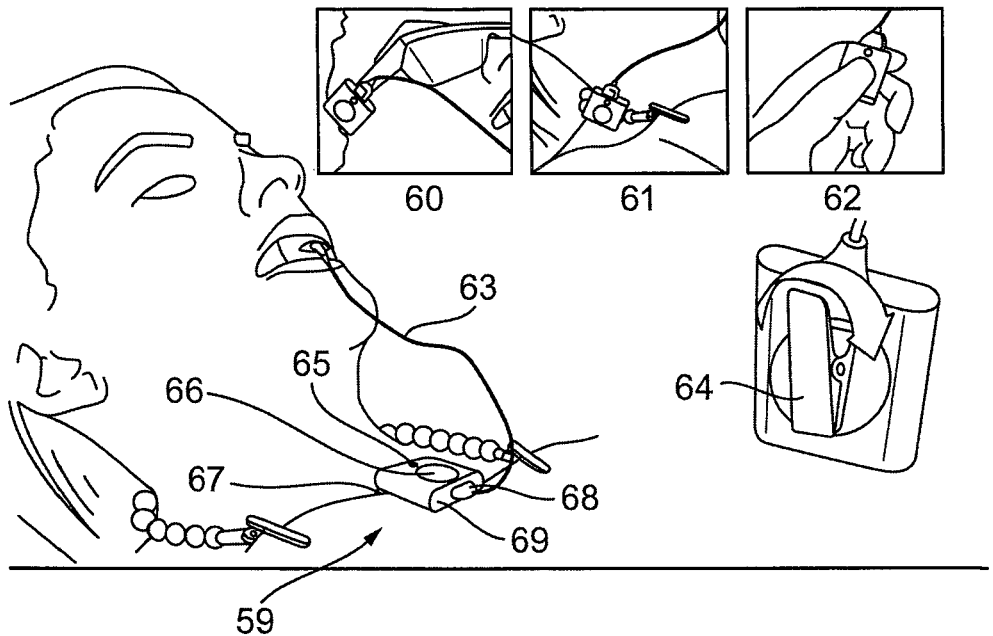
FIG. 38 is an upper perspective view of an embodiment.
Figure 39:
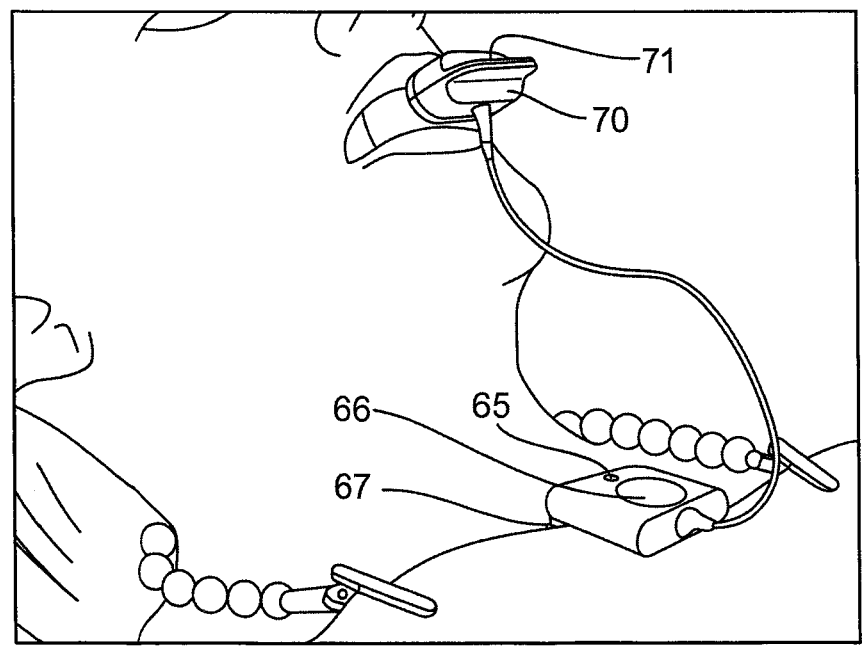
FIG. 39 is an upper perspective view of an embodiment.
Figure 40:
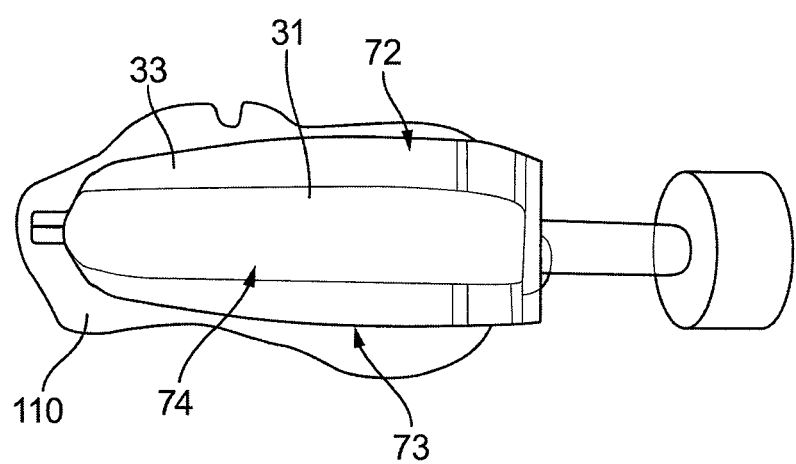
FIG. 40 is a side view of an embodiment.

The activation module(s) 2 can alternatively be charged in a tabletop charging station (not shown) that also acts as a storage place for the modules, which keeps them in a fully charged and ready to use state. A cooling feature (Not shown) may be present in the charging station and can include any suitable cooling mechanism, such as a fan, and that is capable of cooling the activation/illumination module. In one embodiment, a fan may be inserted in the charging station that is arranged to blow air on the attached light engines. The LED trays 8 may be powered by a table top power unit with a power cord connecting the tray and the power unit (not shown). The configuration of an open bite tray 8, FIG. 3 may be similar whether it is an upper, lower, universal upper/lower, quadrant or anterior tray with LEDs 6 embedded in a clear, hermetically sealed tray. Such LEDs 6 can be mounted on a flexible PCB or other suitable substrate. FIG. 38-FIG. 39 show a small light weight, remote power source for the light tray. Such a power source may be clipped to the patient bib 59 or safety glasses 60 or bib chain 61 or just hand held 62.

Figure 32:
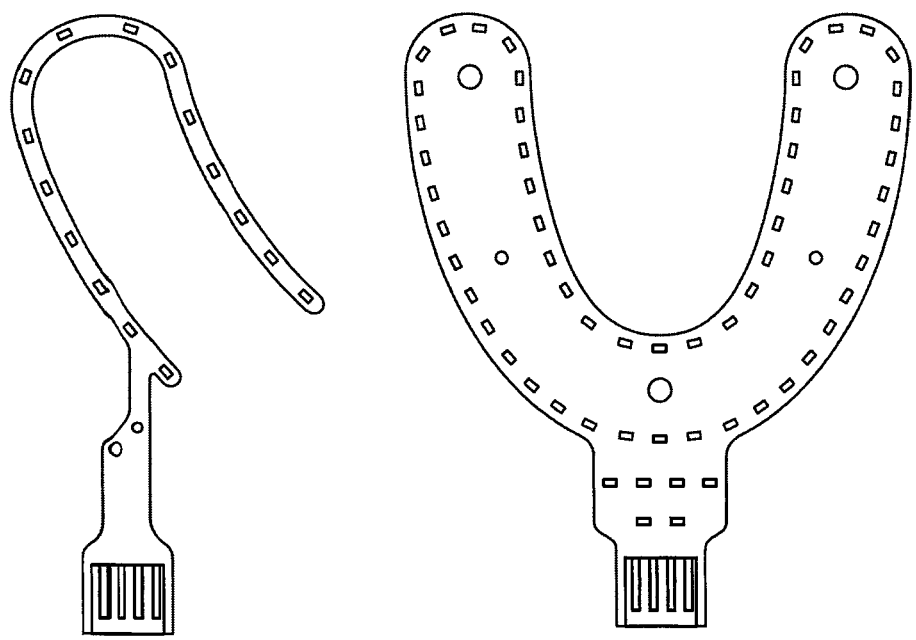
FIG. 32 shows chip-on-board (COB) PCBs used in triple trays and full arch trays.
Figure 33:
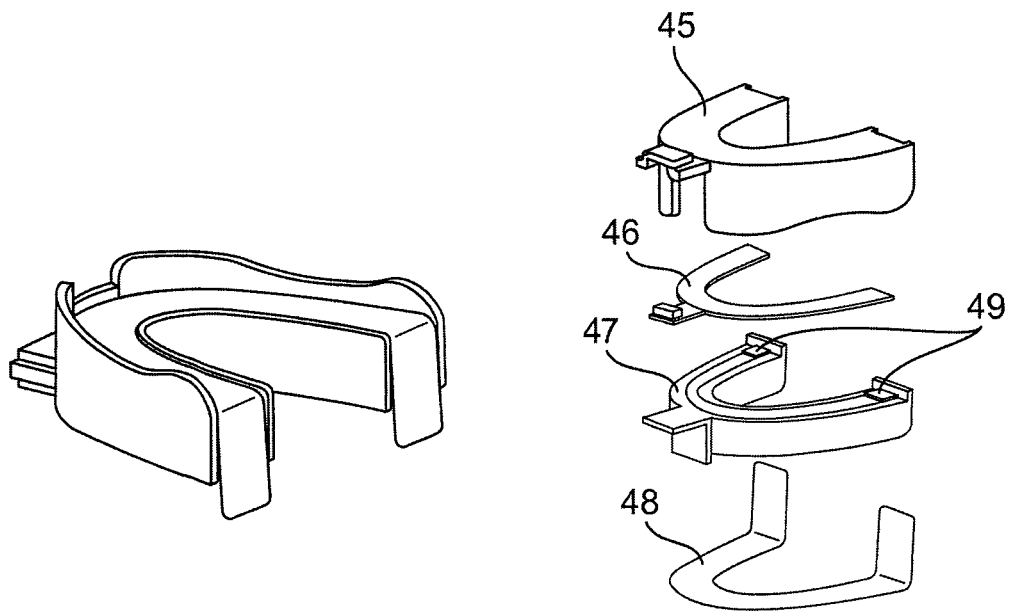
FIG. 33 is an upper perspective view of an embodiment showing one possible construction for a pre-filled full arch tray and the application of a removeable lidstock.
Figure 34:
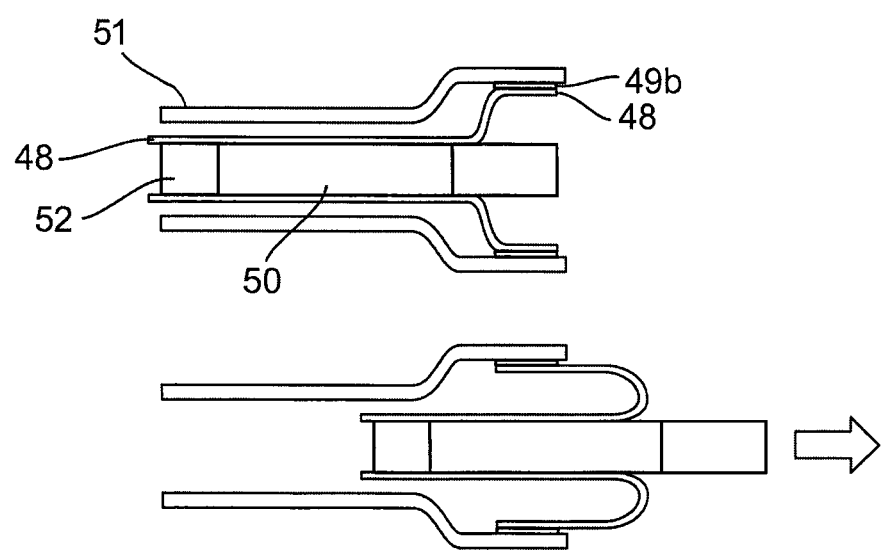
FIG. 34 is a side view of an embodiment showing a pre-filled tray illustrating the concept of peeling the lidstock off at 180° to minimize residue.
Figure 35:
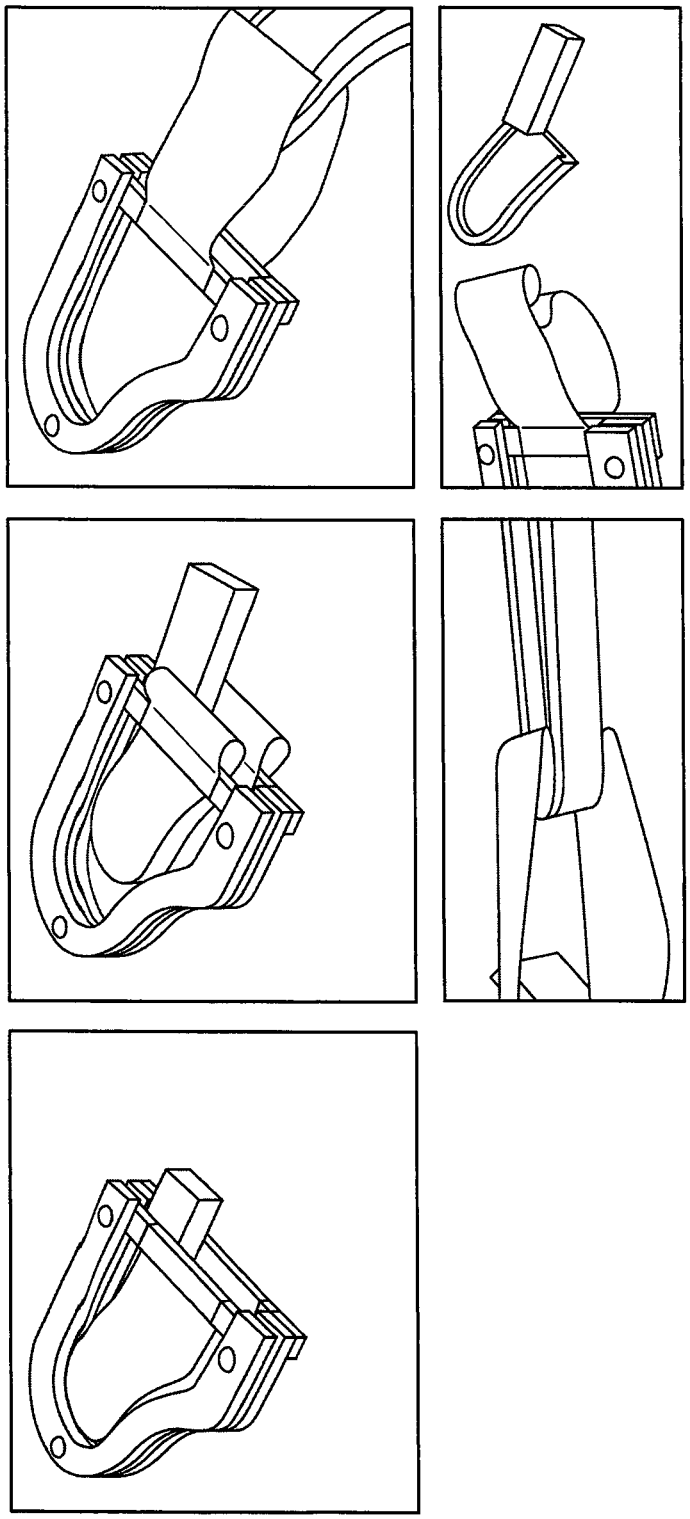
FIG. 35 shows a working model of the concept in FIG. 34.
Figure 36:
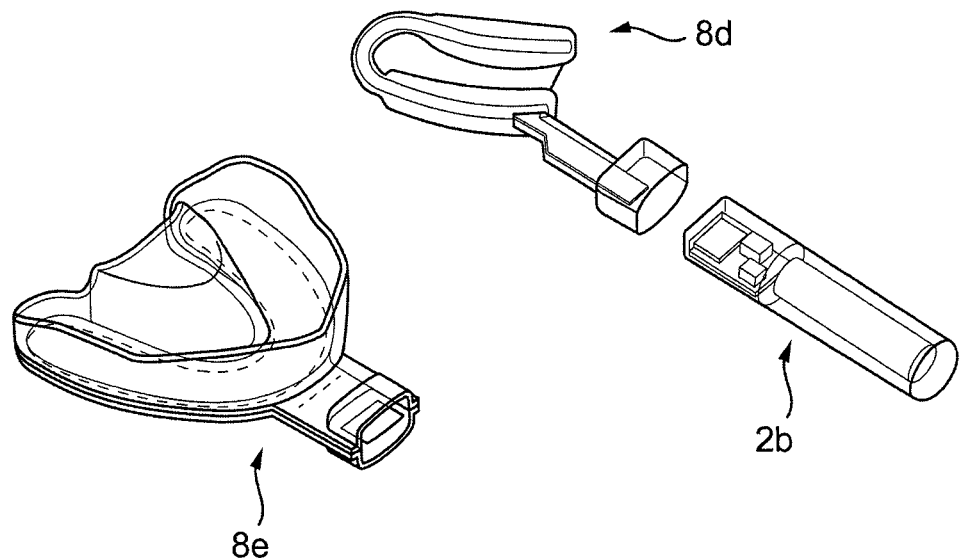
FIG. 36 is an upper perspective view of an embodiment illustrating COB/PCB illumination trays for the full arch and triple tray and the potential activation module with battery source and activation circuit.
Figure 37:
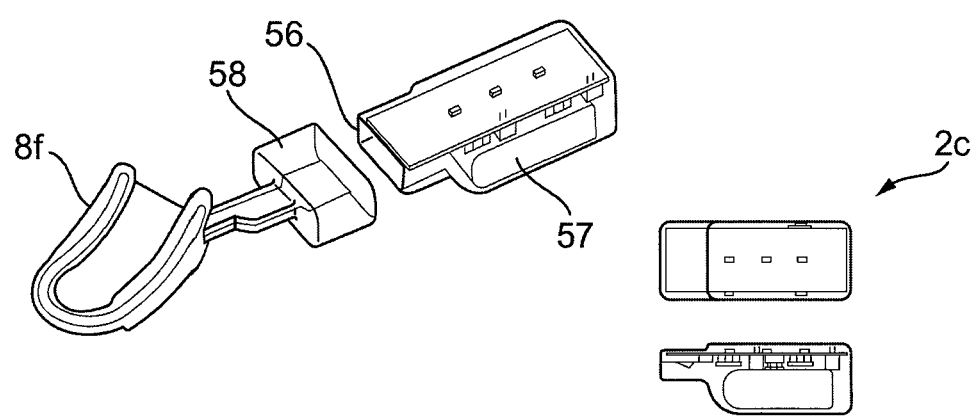
FIG. 37 is an upper perspective view of an embodiment.

In another alternative embodiment, individual LED 6 chips can also be mounted in a configuration known as COB wherein the COB substrate can be formed into a tray like configuration (FIG. 32) similarly to the flexible PCB and hermetically sealed in plastic.

A light emitting tray constructed using COB technology may have individual LED semiconductor dies arranged on for example an aluminum substrate 26 (FIG. 11a) and the substrate is bent into the form of an impression tray (FIG. 11b) and the formed LED substrate 26 is further encapsulated in plastic 10a, 10b (FIG. 11c) to form an LED impression tray as mentioned herein. Alternatively, a light emitting tray constructed using COB technology, may have individual LED semiconductor dies arranged on, for example, an aluminum substrate wherein the flat PCB substrate has notches that allows the board to be bent into smaller or larger arch configurations to accommodate different size trays (not shown). For example, a medium size full arch COB/PCB which fits most patients can be compressed to fit a smaller tray or expanded to fit a larger tray. This would reduce cost because only one size COB/PCB would need to be manufactured as opposed to three different sizes. The COB/PCB could also be a flexible PCB substrate.

Figure 5:
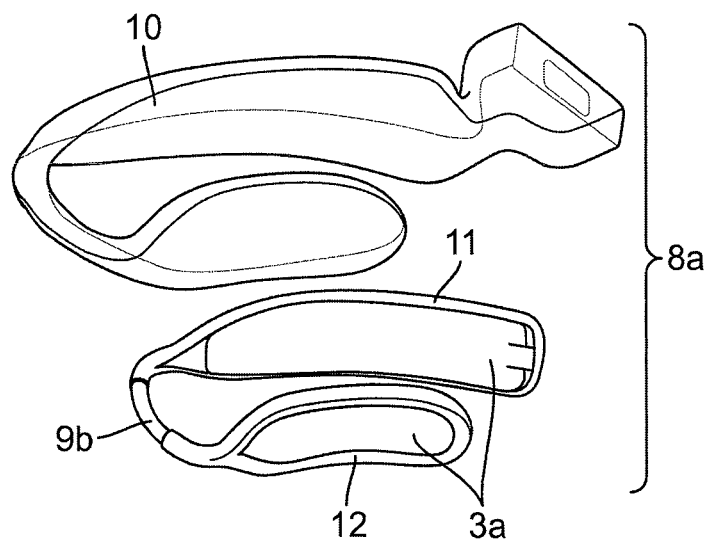
FIG. 5 is an upper perspective view of an embodiment illustrating an assembly concept for a double arch impression LED tray (triple tray or closed bite tray).

A closed bite posterior or quadrant tray 8a may have a buccal vertical wall 11 and a vertical lingual wall 12 joined by a retro molar bridge 9 (FIG. 6, Assembled) in accordance with another embodiment of the disclosure. The bridge 9 would be of sufficient thickness to allow the patient to close their bite in full occlusion and yet be strong enough to support the lingual section 12 of the tray. The LED tray has an internal metal frame for strength (FIG. 5, lower image). The frame is welded together and consists of a buccal sheet metal frame a metal tube 9b that provides rigidity to the retro molar bridge and a lingual sheet metal frame. The buccal and lingual frames each support a flexible PCB 3a with LEDs. The two flexible PCBs are electrically connected by wire leads that run through the metal tube 9b. The frame and PCB subassembly may be hermetically sealed in clear plastic. The closed bite tray is similarly configured for use with an activation module 2.

Figure 6:
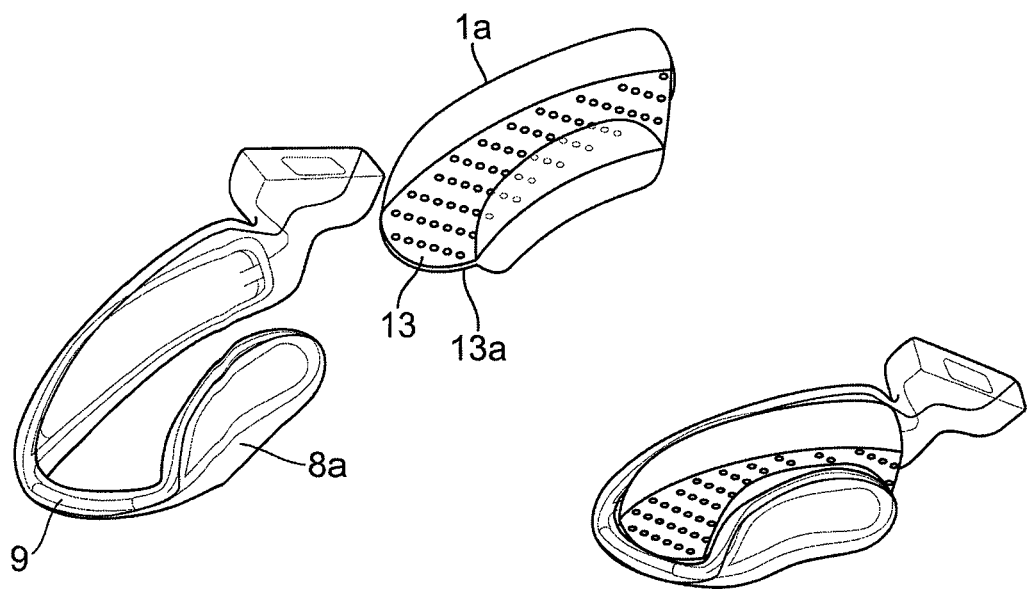
FIG. 6 is an illustration of reusable double arch LED impression tray and the prefilled tray insert (impression material not shown).

Further, the closed bite LED tray 8a may have a means for sliding a prefilled closed bite tray insert 1a into it which contains the light cured impression material (FIG. 6, impression material not shown). The closed bite tray insert 1a may have a fabric mesh middle layer 13 and may be filled with impression material on the top and bottom arches. In cross section the prefilled tray insert 1a would be H-shaped with the horizontal portion being the fabric mesh and the vertical legs being the buccal and lingual walls of the prefilled insert. In embodiments, a thick transparent occlusal mesh may be used as the middle layer or in addition to the fabric mesh middle layer 13 in order to increase the light penetration in the interdental occlusal area. Such a feature may assist in curing of the impression material between occlusal surfaces of opposing teeth. The translucent mesh may be made thicker than conventional occlusal mesh available in popular commercial dual arch trays, for example, the thicker translucent mesh may have a thickness of 0.3 mm to 2.5 mm or 0.4 mm to 2 mm. This thickness helps light travel between opposing teeth and therefore increase the light density in difficult to reach areas to ensure proper curing. Tight occlusal contacts, for example tight intercuspation, may significantly decrease the light density between opposing teeth because light transmission within the tooth structure may be low, and in the case of opaque restorations (metallic, opaque ceramics, or the like) the light is simply blocked. The insert 1a would also have a plastic retro molar bridge 13a, which connects and supports the buccal and lingual side walls. The retro molar bridge of the tray insert 1a would be shaped as to conform with the retro molar bridge of the LED tray in order to maintain a thin profile that does not interfere with full occlusion. The closed bite tray insert may be packaged in a light protective package and have a peel-able protective cover that does not stick to the impression material.

Figure 49:
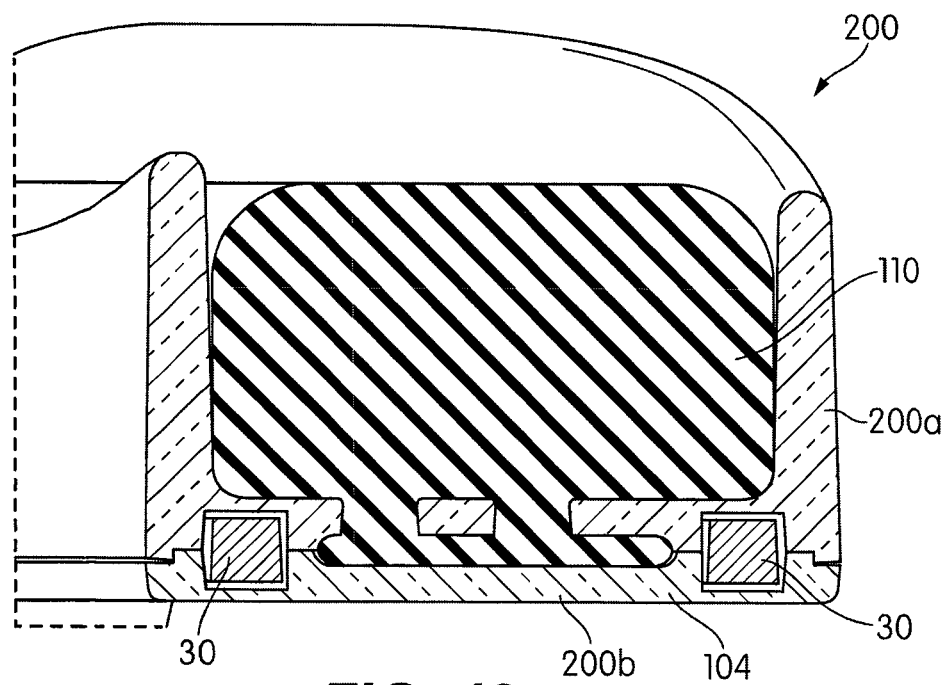
FIG. 49 depicts a cross section of a single arch tray, pre-filled with impression material that is interlocked with the mechanical retention holes

Furthermore, the reusable tray insert 1a may have mechanical retention features 100 such as holes, dovetail slots or T-slots to eliminate the need for tray adhesive. Retention holes in the disposable full arch (open bite) tray, are created in order to create a highly retentive layer at the bottom of the impression tray plate. The two layers are assembled together using ultrasound for example, there are no spills of material 101 on the exterior of the tray with this assembly since the impression is contained in the tray dimension by the external wall of the tray FIG. 49.

An LED tray (not shown) may be constructed from a semi-flexible material such as silicone rubber and a rigid tray insert. The flexibility of the LED tray assisting the assembly and adaptation to the rigid tray insert so that the LED tray can be inserted into a rigid tray having undercuts that could not be otherwise fit.

Figure 41:
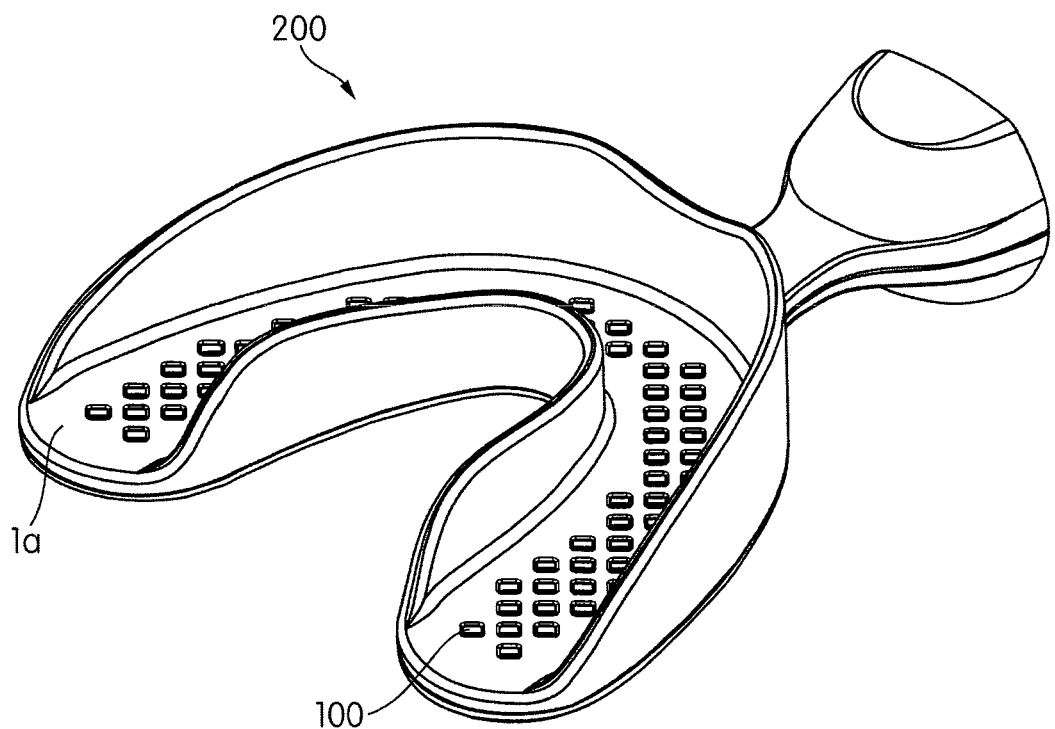
FIG. 41 is a perspective view of a full arch impression tray.
Figure 42:
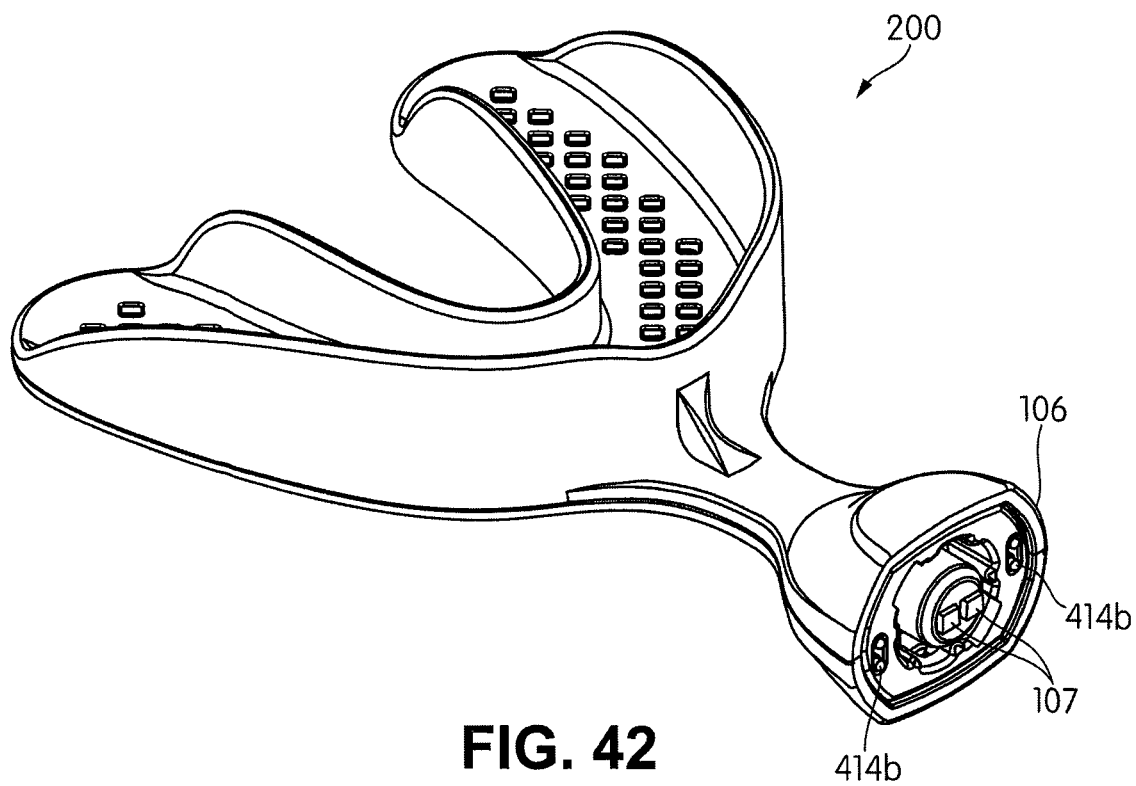
FIG. 42 is another perspective view of a full arch impression tray demonstrating the connector portion.

One of ordinary skill in the art will understand that the entire impression material tray may be disposable as shown in FIG. 42, such that the tray insert 1a is integrally attached to and part of the disposable tray as a whole. In embodiments, the tray 200 of FIGS. 41 and 42 includes a connector portion 106 that connects to a light source. A single disposable tray is shown in FIGS. 41 and 42. The disposable tray of this embodiment may be pre-filled or filled by the dentist immediately prior to use. The mechanical retention features 100 are placed such that when the impression material is in the tray, and the filled tray is placed in a patient's mouth, the impression material will flow through the mechanical retention features and there will be impression material on both sides of the features 100. When the impression material is cured, these mechanical retention features 100 will assist in the cured impression material remain in the tray versus being suctioned to a patient's dentition.

Figure 43:
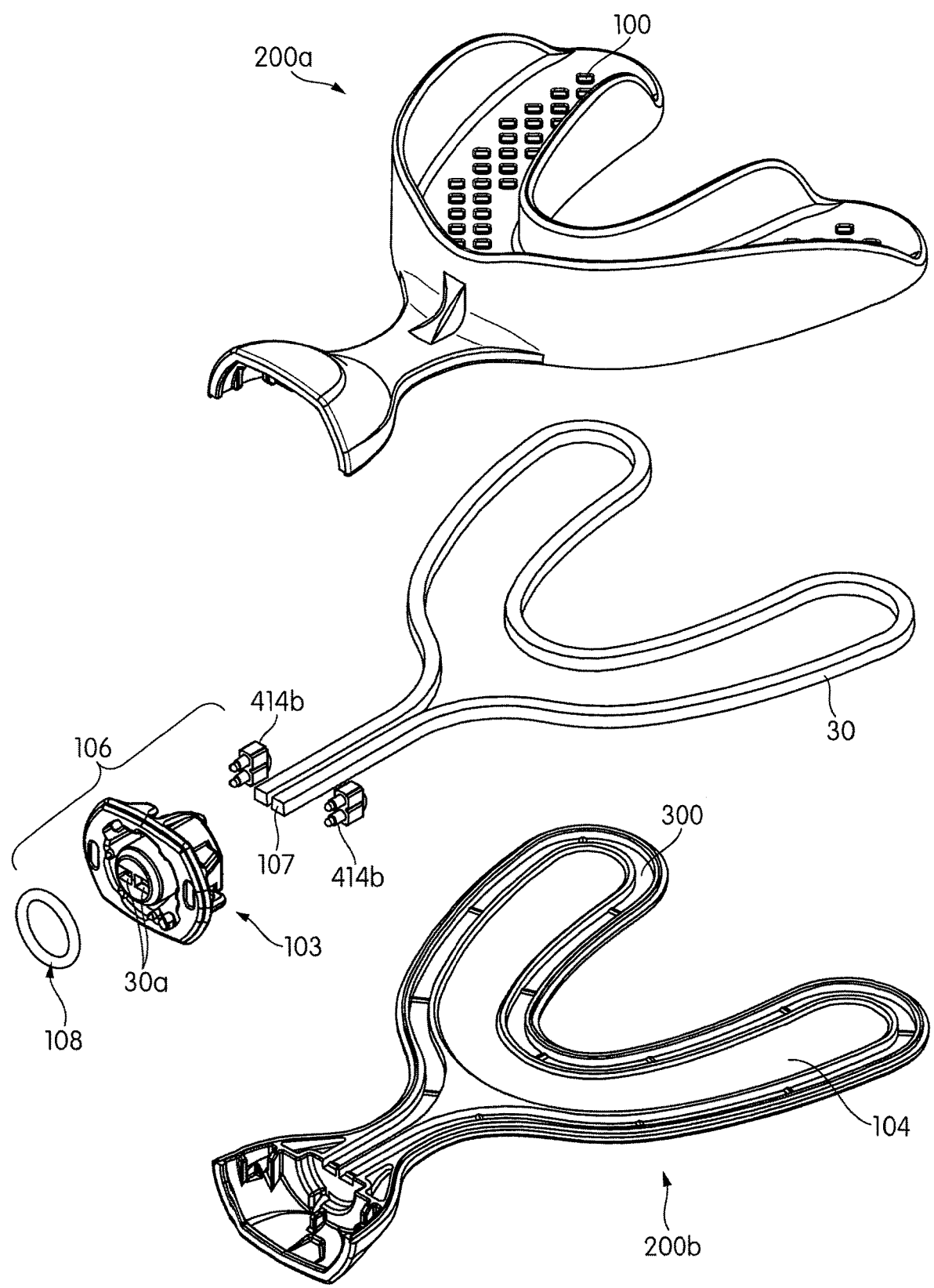
FIG. 43 is an exploded view of one embodiment of a disposable full arch tray.

FIG. 43 shows and exploded view of an integrally constructed full arch impression material tray 200. Although tray 200 is shown and described as a full arch tray, one of ordinary skill in the art will understand that a similar and corresponding construction is possible for a triple tray. However, in a triple tray, the light pipe 30 has only one end in the connector portion 106.

In FIG. 43 it is apparent how the disposable tray may be constructed. In this embodiment, a light pipe 30 is used as the illuminator or light emitter in the tray and is sandwiched between an upper portion 200a and lower portion 200b of the tray. The bottom portion 200b has a groove 300 in which the illuminator or light pipe 30 is located. As one of ordinary skill understands, this groove 300 can be any shape or geometry to support the illuminator or light emitter used in a particular design. The upper portion 200a includes mechanical retention features 102 that assist in retaining the cured impression material within the tray. The upper portion 200a and the lower portion 200b of the tray 200 may be integrally connected to each other in any suitable matter so long as the two portions will not separate. These two portions when connected not only support the illuminator but also the connector portion 106. The connector portion includes a pin 414b on each side of coupler core 103. This coupler core 103 is able to connect to light source such that the illuminator, in this embodiment a light pipe 30, is capable of curing impression material that is added into the tray. The retaining ring 108, such as an o-ring, assists in holding the connector portion 106, illuminator or light pipe 30, the upper portion 200a and lower portion 200b in place. The coupler core 103 includes at least one recess 30a to correspond to the geometry of the illuminator, such as the light pipe 30.

According to yet another embodiment of the disclosure, a disposable tray has a removable and rechargeable battery module for illumination. The tray may be prefilled with light curable impression material 110. Such a tray would have either surface mount LED's, COB LED's (or other curing light source) arranged in a manner as to optimize the light dispersion and curing efficiency. The activation module 2 may be separated from the reusable LED tray 1, so that the electronics can be removed or detached from the LED tray 1 and disinfected thereby making it immune from the harsh effects of steam sterilization of the LED tray.

In yet another embodiment, a light tray 8*b* has a plastic molded light pipe 30 embedded in the tray for light dispersion. The light source or light engine or battery may be external to the tray 8*b* and may be connected to the light pipe tray by direct connection or through a fiber optic light tether (not shown). In other embodiments, the light source may be connected directly to the tray via the connector portion 106 of a tray. Alternatively, a plastic impression tray with a light pipe 30 embedded in the tray for dispersing the light around the dental arch may be achieved. Such a tray may use a reflector 31 to direct the light towards the dentition and improve light dispersion. The reflective material could be made of a metallic mirror coating made by sputtering, vacuum deposition, in-mold labeling, painting, over molding or other coating method known in the art to create mirror like coatings. Such a reflector does not have to be a mirror surface and can be any light reflective or dispersive coating. The light pipe 30 could be a molded plastic component or a flexible fiber optic cable. It may have clear housings 33 to allow for the free transmission of light inside and outside the tray and to allow for curing of overflow material that overflows the borders of the tray. In order to maximize the total light carried and transmitted by the light pipe 30 the cross section of the light pipe 30 is made to closely match the dimensions the surface of the LED emitting surface to maximize the amount of light entering the light pipe. For example a square emitting surface of CREE1950p LED has approximately a 2×2 mm so accordingly, the light pipe may have a cross section of approximately of 2×2 mm. In contrast, using a cylindrical light pipe of 2 mm of diameter when the LED has a square surface area, some of the light of the LED of 2×2 mm emitting surface would simply not enter the light pipe as shown in FIG. 30*b*. Reflective paint may be used outside the housing to redirect light such as back into the tray. Spaces in the reflective coating or uncoated exterior portions of the tray can allow the light to selectively escape to cure overflow material that occurs on the outside of the tray.

Since the painting of the tray may be a multi-step complex procedure, a reflective "snap-on" over tray was devised in another different embodiment. This overtray has the desired profile of reflective coating and can attach firmly to the clear transparent tray. An injection molded part with a plastic with a high content of reflective particles, such as titanium oxide, could constitute this overtray. The reflective coating covering the clear tray can be made translucent or optically semi-permeable with the goal of allowing some light to go through the reflective area and cure some material that may have migrated on the exterior of the tray. Another method to achieve this effect would be to over-mold the reflective layer during the injection molding process for making the trays.

The light source may be external to the tray, perhaps part of a rechargeable module 2*a* comprising a battery 409, driver PCB 406, heat sink 404, and light engine/coupler 35. The light engine 35 may comprise an LED array 34, 6*b*, a glass window 40 and glass light pipe 42 for transmission of light to the plastic light pipe 30 of the tray. A user may disinfect, recharge and reuse the rechargeable/activation module 2*a*. The module may also have a lithium battery capable of delivering, for example, (2-10 W) during activation. Further, the battery or power source and activation circuit may be removed from the tray and positioned remotely in a small handheld unit. It will be appreciated by skilled persons in the art that advantageous features of an LED tray can also be incorporated into the design of a light pipe tray 8*b* and that tray 8*b* is not limited in its application to the details of construction or to the arrangements of the components set forth in the descriptions or illustrated in the drawings.

Figure 45:
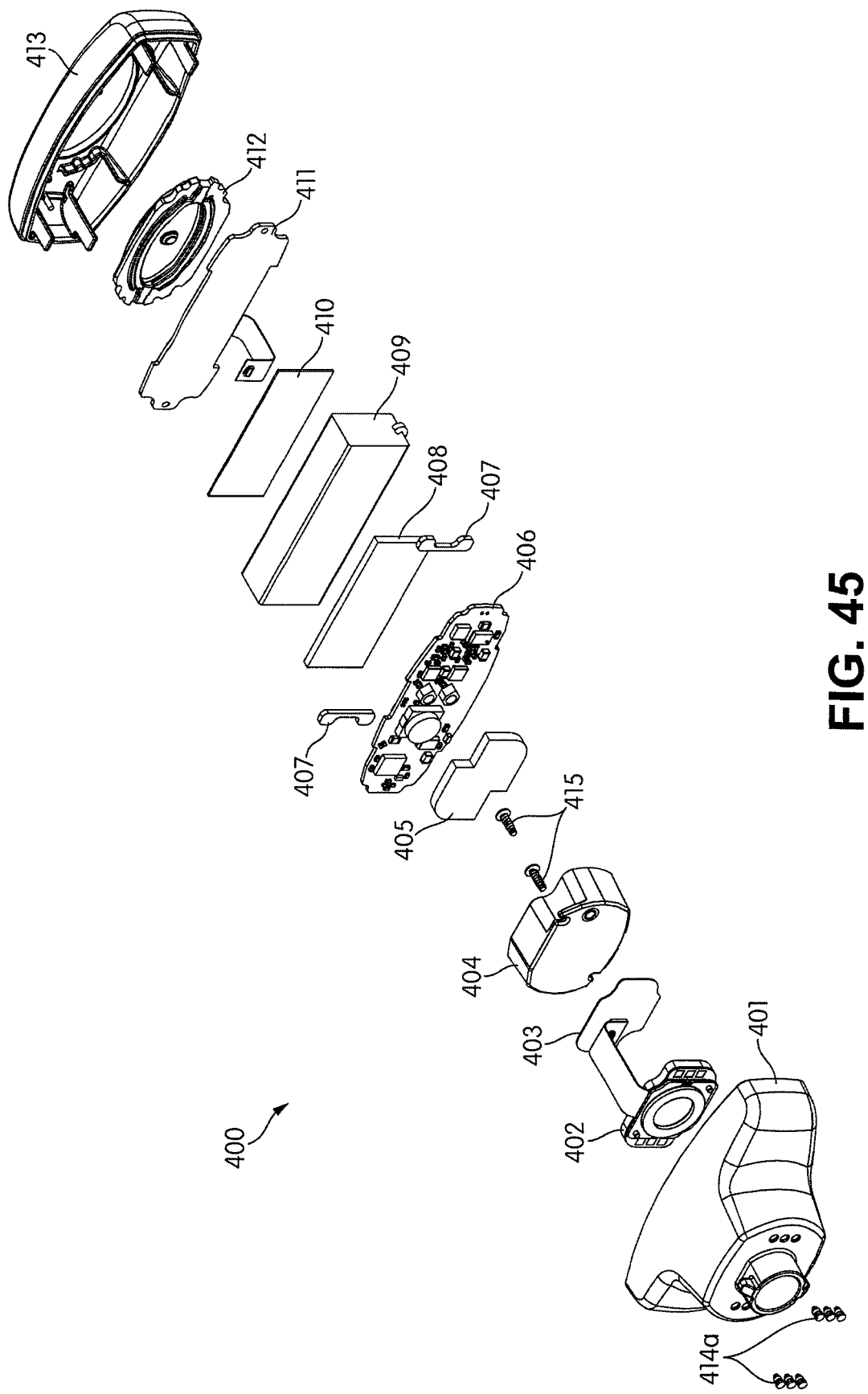
FIG. 45 is an exploded view of one embodiment of a light engine.
Figure 46:
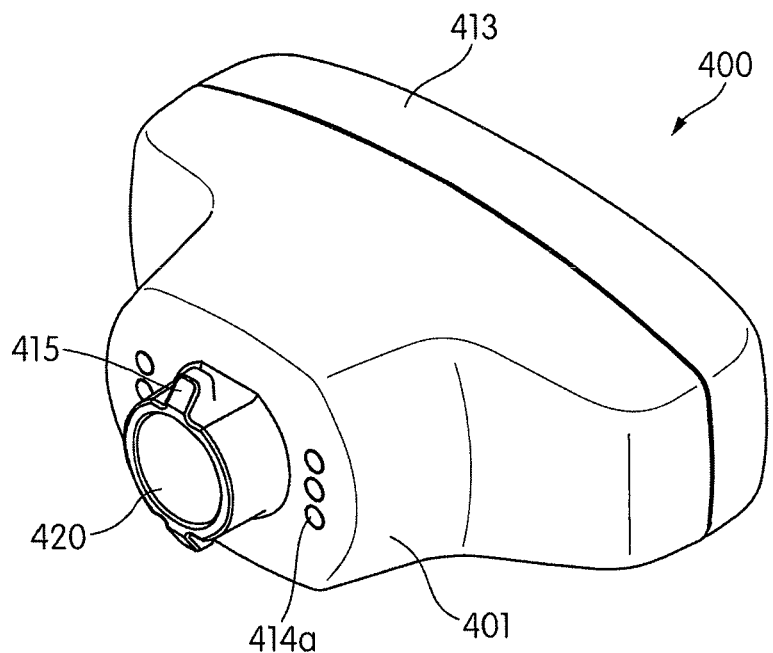
FIG. 46 is one perspective view of one embodiment of a light engine.
Figure 47:
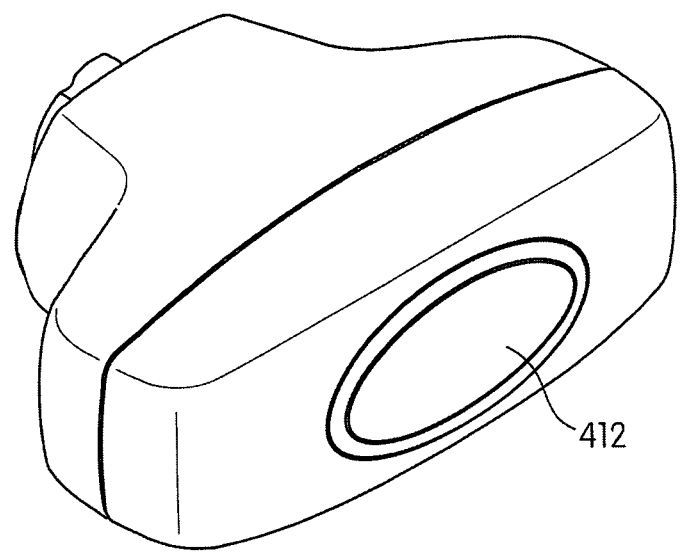
FIG. 47 is another perspective view of one embodiment of a light engine.
Figure 48:
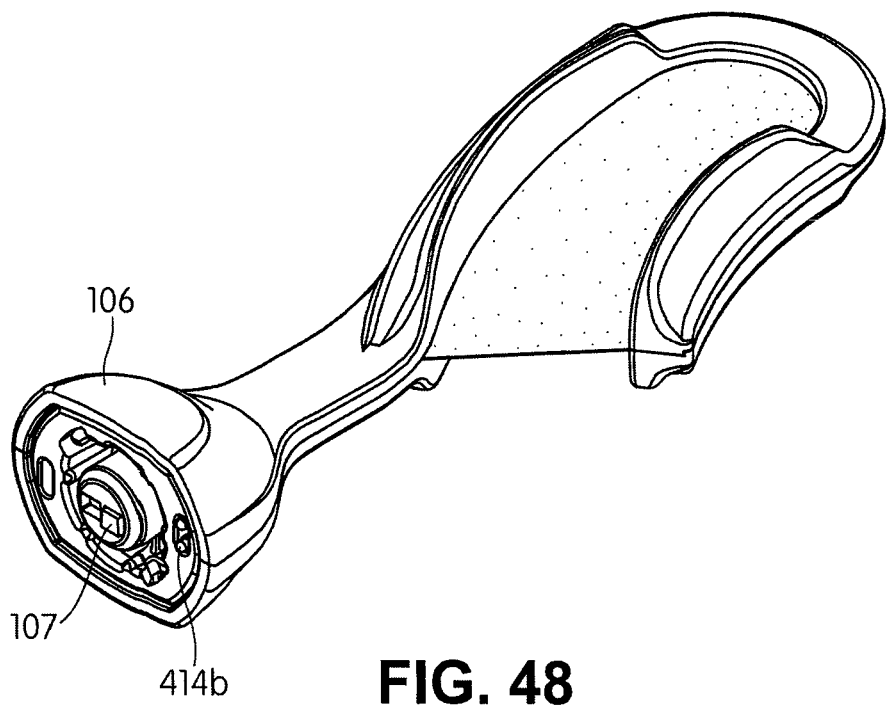
FIG. 48 depicts one embodiment of a triple tray.

In one specific embodiment of the light engine, the light source and battery are located in one housing as shown in FIGS. 45-47.

The light engine 400 housing includes a first portion 401 and a second portion 413.

This housing houses both the battery 409 and the light source 402.

The light source depicted in FIG. 45 is a LED printed circuit board, but any suitable light source could be substituted in this configuration.

This light source 402 can be attached to a LED board thermal transfer tape 403.

As one will understand, the light source 402 must be near a heat sink 404 in order to prevent over heating.

In embodiments the heat sink is a phase change material such as a wax. Any suitable phase change material heat sink may be used.

The heat sink 404 includes a thermal transfer pad 405 which is attached by at least one screw 415.

As is apparent from FIG. 45, the light engine 400 further includes a main printed circuit board 406, a main printed circuit board spacer pad 407, a battery pad 408, the battery 409, a battery mount 410, and button PCB 411, electrical pins 414*a*, and the light engine button 412. In embodiments, the light pipe 30 is placed throughout a tray, such as full arch tray 200 so that the single light pipe 30 has two ends 107 that are visible in the connector portion 106. In different embodiments, the light pipe 30 only has one end 107 apparent in the connector portion 106.

This embodiment can be most useful in impression material trays, such as a triple tray 500 configuration.

The different number of light pipe ends 107 in the connector portion 106 correspond to the number of pairs of pins 414*b* in the connector portion 106.

For example, a single arch tray 200 may have a total of four pins 414*b*, while a triple tray 500 may have two pins 414*b*. This pins match up to or align with the pins 414*a* found on the light engine 400.

One will understand that the number of pins as discussed here for illustration, and any suitable number of pins may be present.

Figure 44:
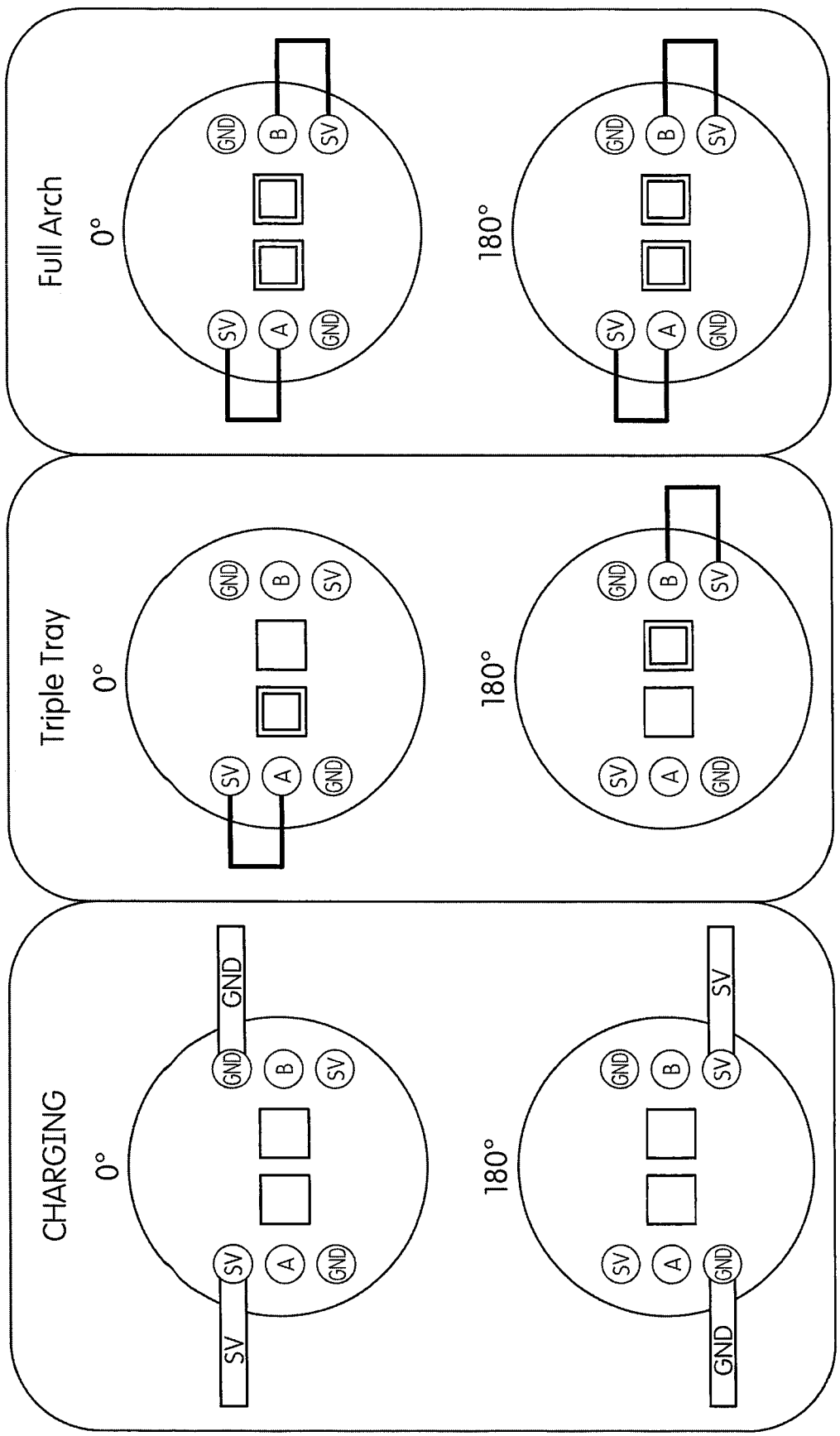
FIG. 44 is a schematic diagram of a connector portion of a light engine showing the contacts and possible electrical connections with the tray contacts to determine whether it is connected to a charging station, connected to a full tray, or connected to a triple tray.

FIG. 44 demonstrates one embodiment where due to the contact between the pins 414*a* on the light engine 400 and the pins on the impression tray, either triple tray 500 or full arch tray 200, the correct number of LEDs are lit in order to irradiate in the light pipe 30.

FIG. 44 is specifically showing one embodiment where the light engine contact portion 420 is shown.

In this embodiment, the light engine 400 includes a rechargeable battery. Also, referring to the light engine pins in FIG. 44 as first SV, second SV, A, B first GND and second GND. When the light engine is on a charging station, the first SV pin of the light engine is aligned with the SV lead on the charging base and the first GND pin of the light engine is aligned with the GND lead of the charging base. This alignment permits charging of the battery in the light engine. When the orientation of the light engine is turned 180 degrees the second SV pin of the light engine is aligned with the SV lead on the charging base and the second GND pin on the light engine is aligned with the GND lead on the charging base and likewise permits battery charging. The unique arrangement shown in FIG. 44 permits the light engine to be attached in two orientations and still make the correct connections, so that the user does not have to ensure a specific alignment for proper function.

Contacts on the trays connect contacts on the light engine in electrical continuity. When a triple tray 500 is connected to the light engine 400, then the tray contacts connects the either the SV and A pins or SV and B pins of the light engine. When the SV/A connection is made the first LED is illuminated which is correctly oriented to the light pipe in the triple tray. When the light engine is turned 180 degrees the SV/B connection is made and the second LED is illuminated which is now correctly oriented to the light pipe in the new orientation. The light engine 400 thereby recognizes which LED should be activated in order to illuminate the light pipe 30.

Similarly, when a full arch impression tray 200 is connected to the light engine 400, then the first SV pin of the light engine is connected to the A pin of the light engine and the second SV pin of the light engine is connected to the B pin of the light engine. In this configuration, the light engine knows that a full arch tray is connected and that both LEDs should be illuminated. When the connection is turned 180 degrees the same connections are made due to the unique configuration of the pins. Again, the light engine 400 is able to recognize that both LEDs should be activated to properly light the light pipe 30. Based on the number and position of pins 414a that are in contact with the light engine 400, the light engine 400 is able to determine how to properly activate the needed LEDs or to charge the battery.

It should be noted that the cross-sectional shape of the light pipe may correspond or be identical to the geometry of the LED. This can improve the efficiency of the light transmitted into the impression tray.

Figure 30A:
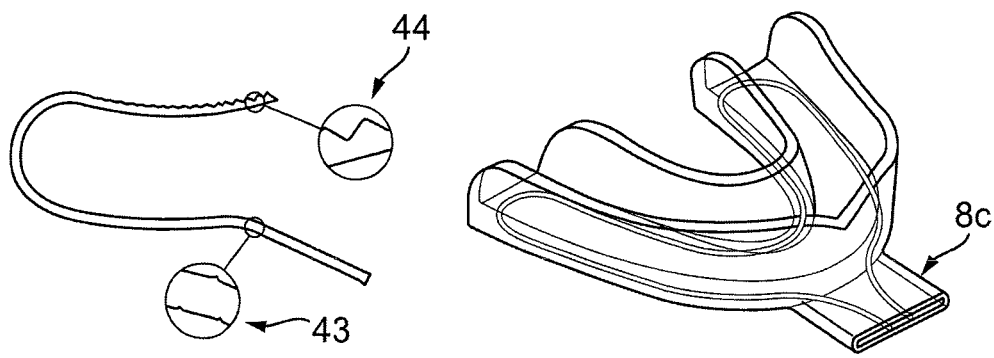
FIG. 30a shows the light pipe with small and large notches to allow light to escape and how the light pipe is configured into a full arch tray.
Figure 30B:
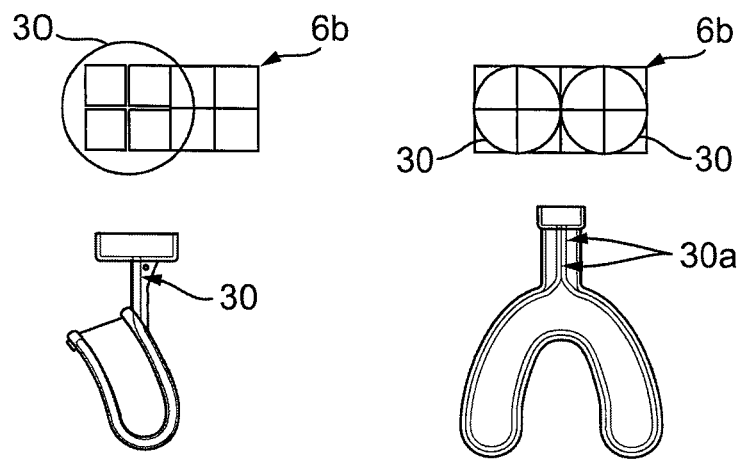
FIG. 30b shows how the light pipe is configured to capture light from the LED array in the light engine and configurations for triple and full arch trays.
Figure 30C:
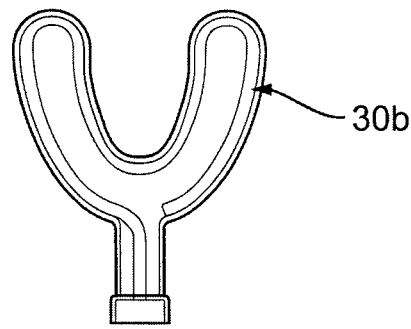
FIG. 30c shows an alternative construction for a full arch tray with one light pipe
Figure 31:
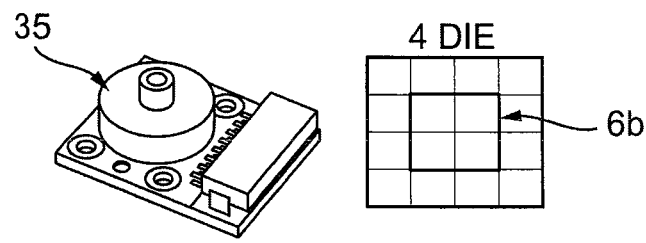
FIG. 31 illustrates one example of an LED light engine used for the light pipe trays as shown in FIGS. 30b and 32c.

Turning to FIG. 30.*a*, the light pipe may have notches 43, 44 of different sizes to let out light at precise locations, for example, small notches closer to the light source to minimize light extraction where light density within the pipe is high and larger notches further away from the light source to maximize light extraction where light density within the pipe is lower thus evening out the light dispersion throughout the impression tray. This is advantageous because the direction of light can be controlled to cure impression material at hard to reach areas. Alternatively paintings or reflective coating may be used on the surface of the light pipe to control the exit of light from the light pipe.

In another embodiment, a disposable light tray system is disclosed. In such a system there is no need for a tray insert. The light source tray may be economical and low cost at high manufacturing volumes and it would be more economical to dispose of the tray than reprocess it for use with another patient. The light source tray may be prefilled with the light cured impression material, covered with a protective film and packaged in a light proof package.

Figure 7:
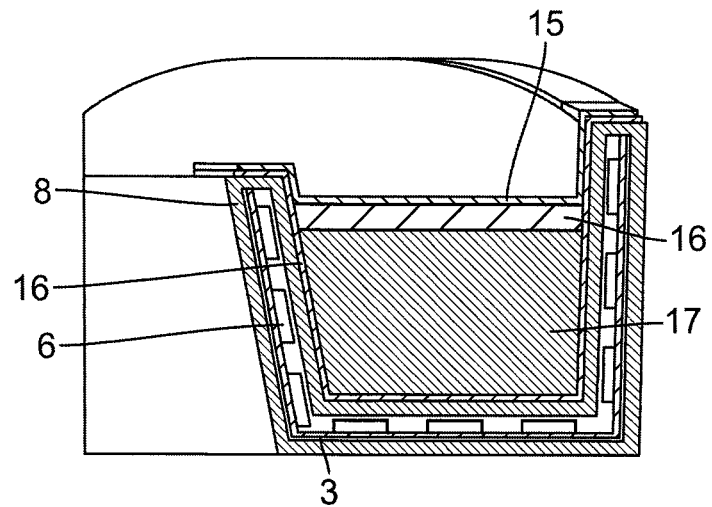
FIG. 7 is a cross section of a prefilled tray insert and LED tray showing a layered filling technique with a thin viscosity (light body) wash material and thicker viscosity (heavy body) tray material.
Figure 8:
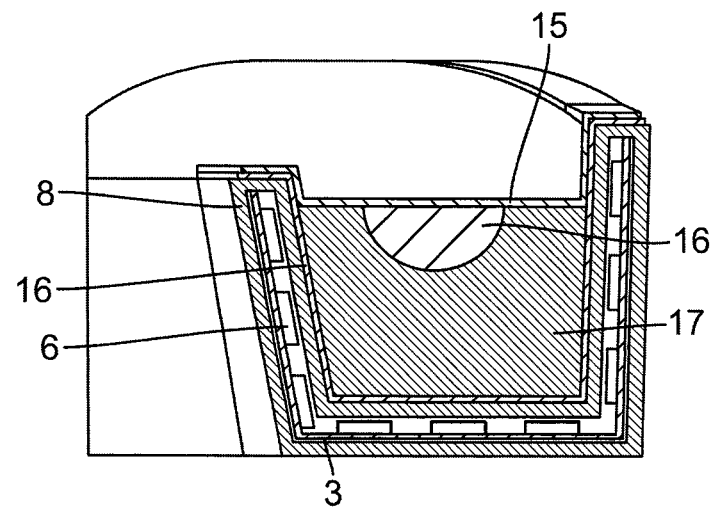
FIG. 8 is a cross section of a prefilled tray insert as in FIG. 7 except the tray material is formed into a trough for the light body.
Figure 11A:
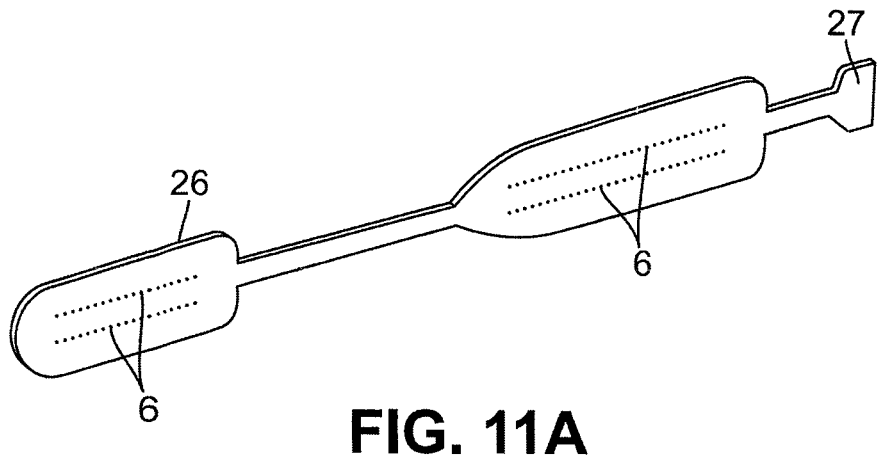
FIG. 11a shows an aluminum substrate with individual LED semiconductor dies in a preformed flat for a double arch tray (i.e. chip on board LEDs).
Figure 11B:
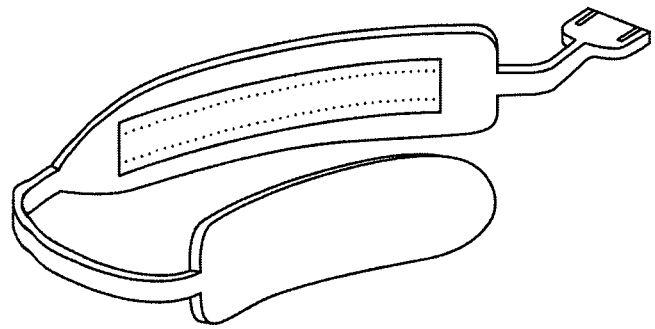
FIG. 11b shows the aluminum LED substrate of FIG. 11a bent into the form of a double arch impression tray prior to plastic encapsulation.
Figure 11C:
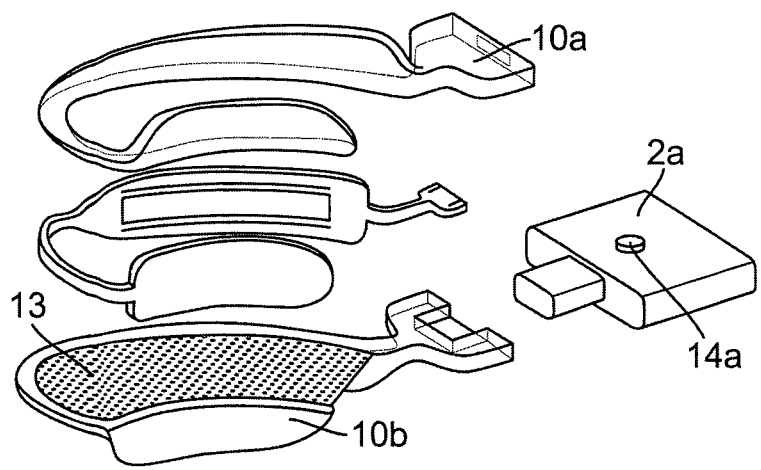
FIG. 11c shows the plastic encapsulation of the substrate in FIG. 11b.
Figure 12:
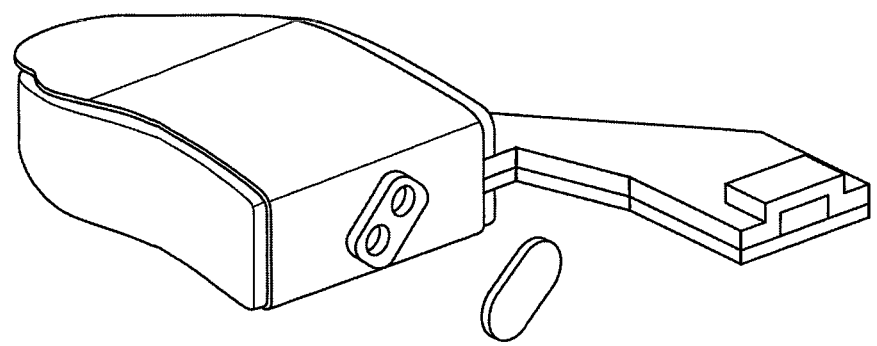
FIG. 12 is an upper perspective view of an embodiment. It shows a concept for sealing a triple tray with a lidstock that has a filling port in the anterior section of the tray, one port for the upper portion of the tray and one for the lower portion of the tray with a fabric mesh separating the upper and lower halves.
Figure 13:
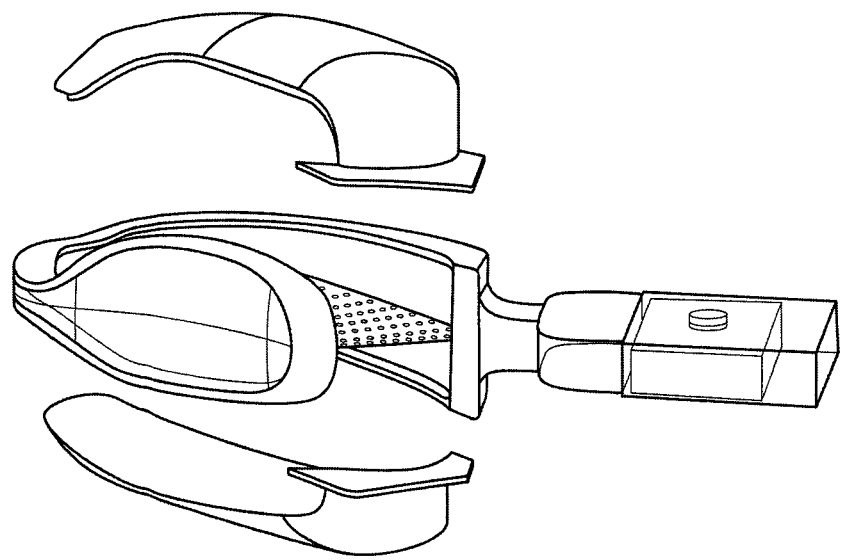
FIG. 13 is a perspective view of an embodiment showing a co-injection molded lidstock that is sealed to the upper and lower walls of the triple tray, which is remove-able to expose the pre-filled tray material (not shown).
Figure 14:
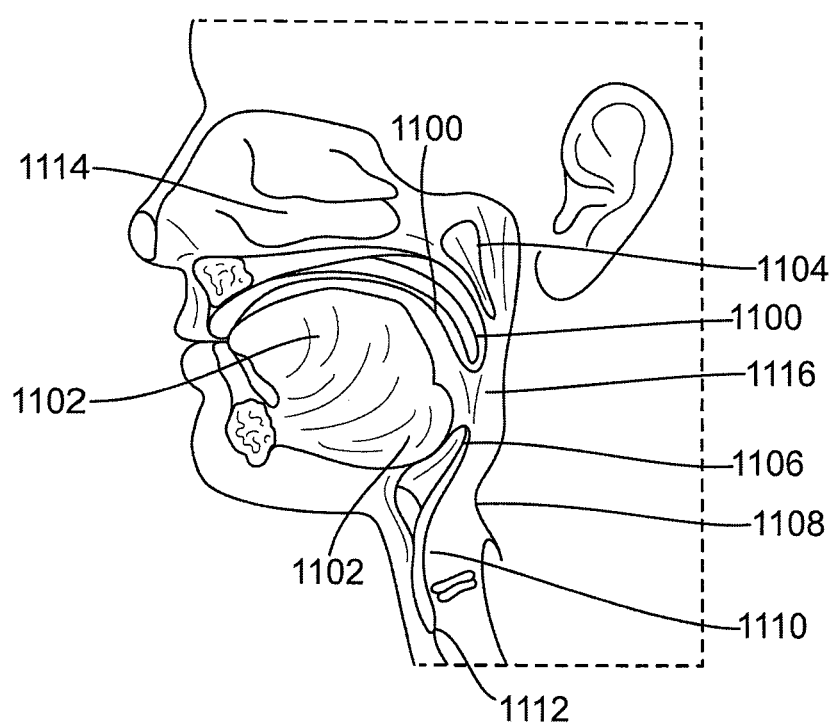
FIG. 14 is a diagram of the dental anatomy indicating soft palate and tongue areas that are prone to overflow and hard to cure.

An embodiment described herein is a prefilled tray insert 1b with layered light 16 and heavy body 17 (horizontal layers of uniform thickness or a heavy body 17 trough shaped layer with a light body 16 filling, as shown in FIGS. 7 & 8). In this embodiment, the user such as a dentist or hygienist does not have to apply wash material to the prepared tooth saving a valuable step, because such wash material is prefilled in the tray with the heavy body. For example, such an impression could be suitable for the first impression of a provisional (temporary) crown. Alternatively prefilled impression tray with a posterior border of clear putty viscosity impression material 18 will reduce overflow of the heavy body tray material 19 into the retromolar, lingual vestibule or soft palatal areas of the mouth (shown in FIG. 9).

As one of ordinary skill in the art will understand, the differences between heavy body and light body impression materials are well known to a skilled hygienists and dentists. Specifically, ISO 4823 specifications detail the consistency of putty (type 0), heavy (type 1), medium (type 2) and light (type 3). As used herein, putty and heavy body may have a consistency of below 40, and a light may have a consistency of above 30.

An LED curing tray with lenses 20 on the inner surface 22 of the reusable tray that focus or disperse the light 28 from the LEDs 6 as needed to efficiently provide adequate intensity to specific areas of the impression and oral cavity (shown in FIG. 10). Dispersion lenses 23 allow LEDs to be spaced further apart than would normally be needed due to the angle of light emittance. Focusing lenses 24 allow LEDs 6 to cure in deeper areas, for example in overflow areas that would not receive enough light from LEDs 6 with dispersed light.

According to another embodiment, a curing tray has a programed circuit that illuminates the LEDs 6 (or other curing light source) in a sequence that reduces the overall current needed to drive groups of LEDs 6 in various regions of the tray. For example, as described in Dentsply Caulk Genesis™ Clinical Technique Guide, the posterior border of the tray could be cured first to reduce overflow into the soft palate, then the occlusal surface could be cured to fully stabilize the tray, then the palatal area, then the buccal surface, thereby reducing the current demands on a battery of the activation module 2. Alternatively, the tray may illuminate said LEDs at different time intervals and intensities to cure the various thicknesses of material in said tray and to reduce heat generation.

A universal top and bottom arch LED tray and tray insert may be manufactured such that the upper palate of an upper impression tray is removed so that it can be also used as a lower tray and the lingual anterior wall is angled away from the teeth so as to clear the upper palate when used on the upper arch (not shown).

In yet another embodiment, the device may contain a temperature sensor (not shown), so that either the illumination time and/or intensity can be regulated to reduce intraoral temperature and prevent thermal damage to the teeth.

In accordance with yet another embodiment, the device has two or more peak wavelengths for curing materials with multiple photoinitiators, for example one type of LED 1 (or other curing light source) with a wavelength from 350 to 410 nm and another type of LED (or other curing light source) with a wavelength from 450 to 490 nm in order to improve curing efficiency and reducing for example the oxygen inhibited layer that can form on the surface of some dental materials. An LED curing tray may have a variety of LEDs with wavelengths ranging from 200 to 700 nm.

Moreover, the power distribution and placement of the LEDs may be varied to provide a greater intensity to thick areas of the impression 118, 122, 124 and lower intensity to thinner areas of the impression.

Further the tray may be configured for the treatment of peri-implantitis and periodontal disease. During periodontal treatments, plaque is removed mechanically by scaling and root planning. Typically antibiotics are administered to the periodontal treated site. However development of resistance against antibiotics and side effects of the drugs is common. Photoactivated antimicrobial therapy is an option. A photosensitizing solution is first applied to the treated site. Typical photosensitizers are methylene Blue and other dyes, as well as photoactive nanoparticles such as titanium oxide. The photosensitizers are activated by light and release singlet oxygen and other reactive oxygen species known to be highly toxic against microorganisms. Light activation may be accomplished by inserting the reusable tray equipped with LED's (or other curing light source) which may emit in the 650-550 nm region of the light spectrum and killing pathogenic microbes.

Further the tray may be configured to deliver light in the 350-700 nm wavelength region for bio-stimulation of bone and soft tissue and possible reversal of osteonecrosis.

In accordance with another example embodiment, the device is configured for placing and bonding preformed orthodontic wire and bracket assemblies to teeth. In particular, lingual brackets which are especially difficult to position and bond. The light cure impression material is used to construct a positioning matrix in the dental lab during the fabrication of the preformed orthodontic wire and bracket assembly. The cured positioning matrix is then used by the orthodontist to place the wire and bracket assembly on the teeth and light cure the bracket cement by activating the light cure tray and matrix a second time for bonding the brackets that have been accurately positioned.

Photo-curable adhesives are often used in indirect bonding procedures for bonding orthodontic appliances to the enamel surfaces of the patient's teeth. When photocurable adhesives are desired for an indirect bonding technique, it is common practice to fabricate the bonding tray with materials that transmit light in order to facilitate exposure of the photocurable adhesive material to the light and subsequent hardening. However, if an extra-oral light source is used, the presence of a bonding tray in the oral cavity can somewhat hinder the practitioner's ability to maneuver and aim the source of light toward adhesive that is located in certain regions, such as in directions toward appliances that are located in the posterior regions of the oral cavity. With the reusable tray described herein, this can be accomplished very easily since the proper alignment needed is easily maintained and all the brackets can be cured in place simultaneously. Other orthodontic procedures can be easily envisioned as being more advantageously done with a reusable light emitting tray. One example is the placement of lingual retainers.

Further, a light cured impression system that includes a color changing light cured impression material that indicates that curing is complete by changing color may be realized. This is particularly advantageous because areas outside of the tray boundaries such as overflow areas are more difficult to expose to the curing. This gives the practitioner the assurance that all areas are cured before removing the tray.

In alternative embodiments, a light curing impression system that self-disinfects the impression with UV light, so that it can be safely handled is obtained. The tray may have LEDs (or other curing light) in the short-wavelength (UV-C) range that kills microorganisms such as bacteria and viruses and other pathogens. In particular, the wavelength of 250 to 260 nm is effective in germicidal irradiation. The self-disinfection can be initiated after curing and removal from the patient.

Figure 21:
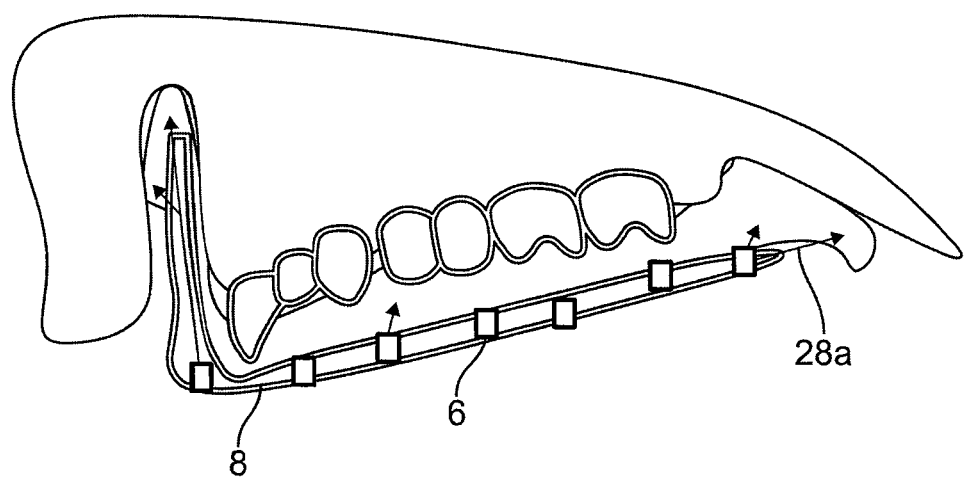
FIG. 21 is an illustration showing how the light must travel through the walls of the tray for optimal curing.
Figure 22:
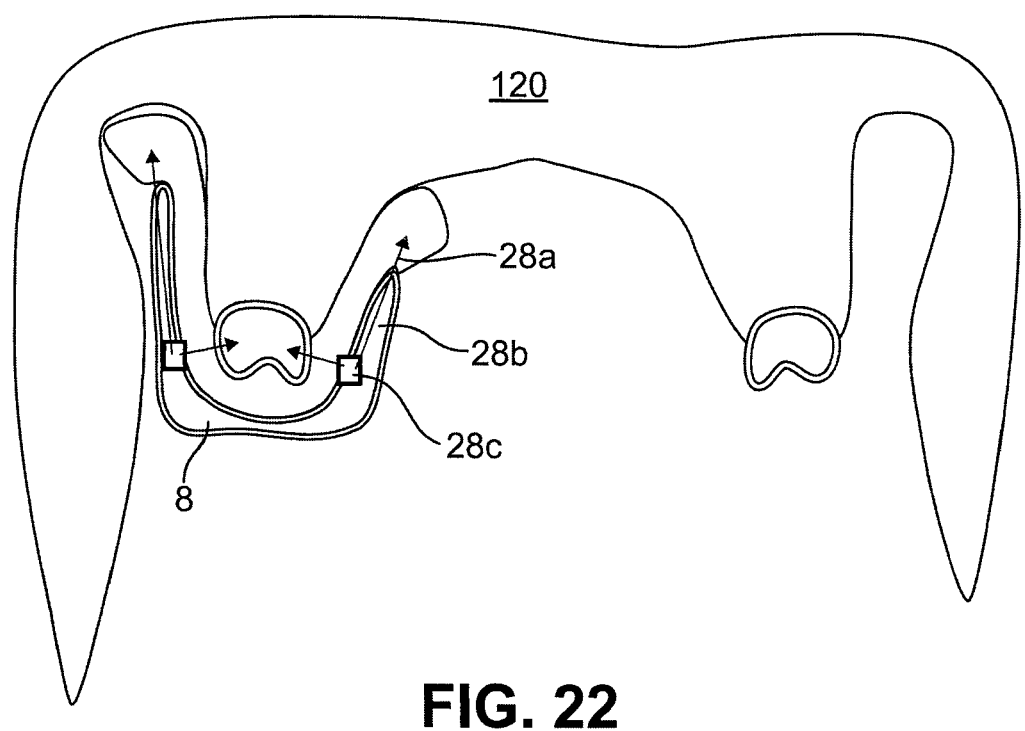
FIG. 22 is an illustration showing how the light must travel through the walls of the tray for optimal curing, which is 90° to the illustration of FIG. 21.
Figure 23:
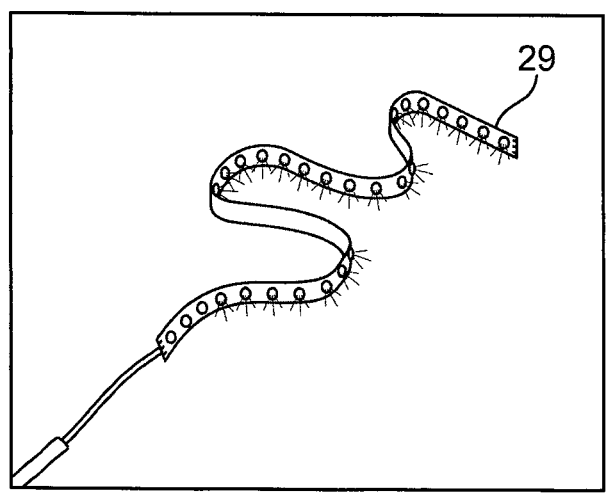
FIG. 23 illustrates a flexible LED strip.
Figure 24A:
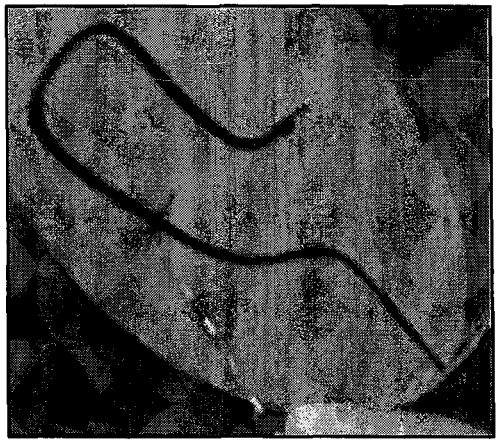
FIG. 24 a shows a first stage of insertion of the strip of FIG. 23 into a channel as could be made in a triple tray.
Figure 24B:
Figure 24C:
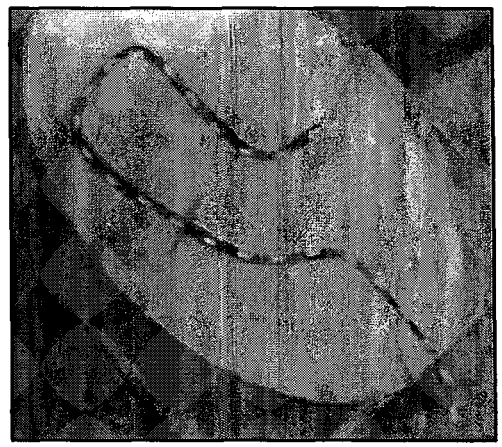
Figure 24D:
Figure 25A:
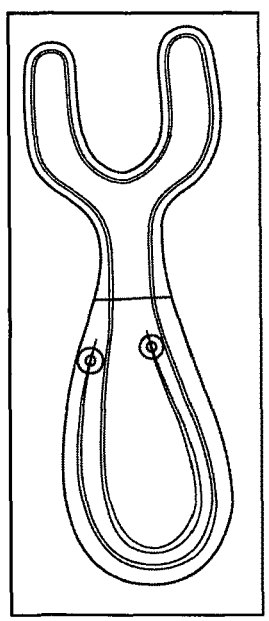
FIG. 25 a shows a first stage of insertion of the strip of FIG. 23 into 2 channels as could be made in a full arch tray.
Figure 25B:
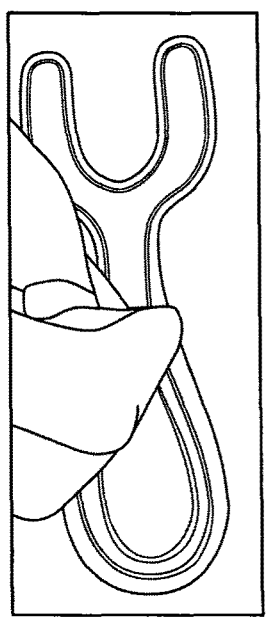
Figure 25C:
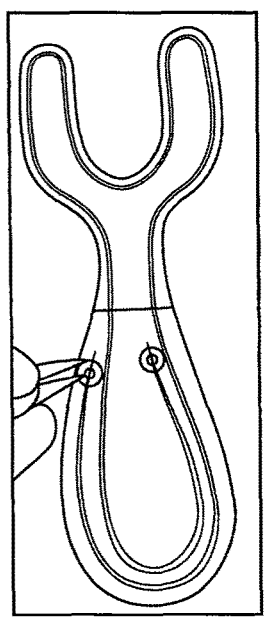
Figure 25D:
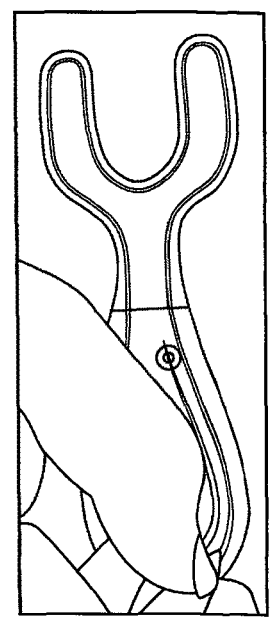
Figure 27:
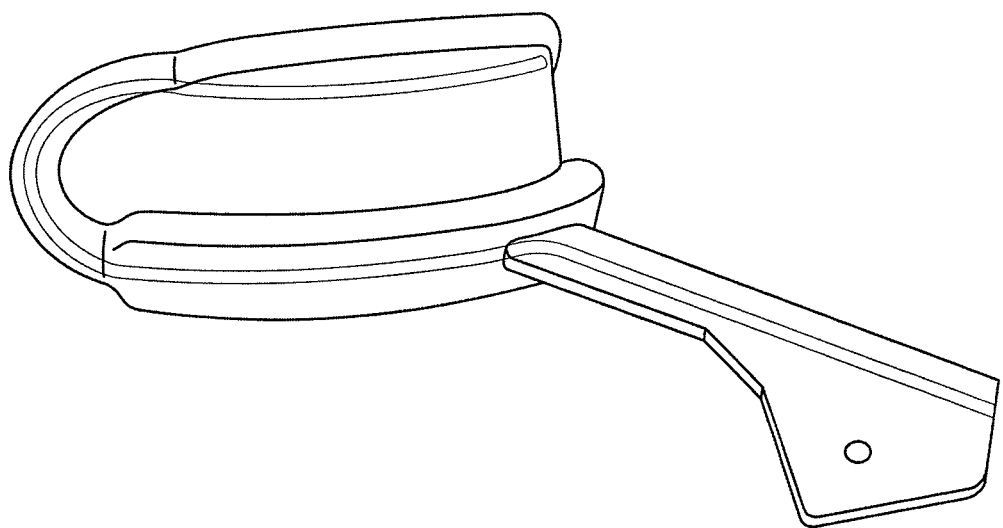
FIG. 27 shows a diagram of a triple tray with a light pipe.
Figure 28A:
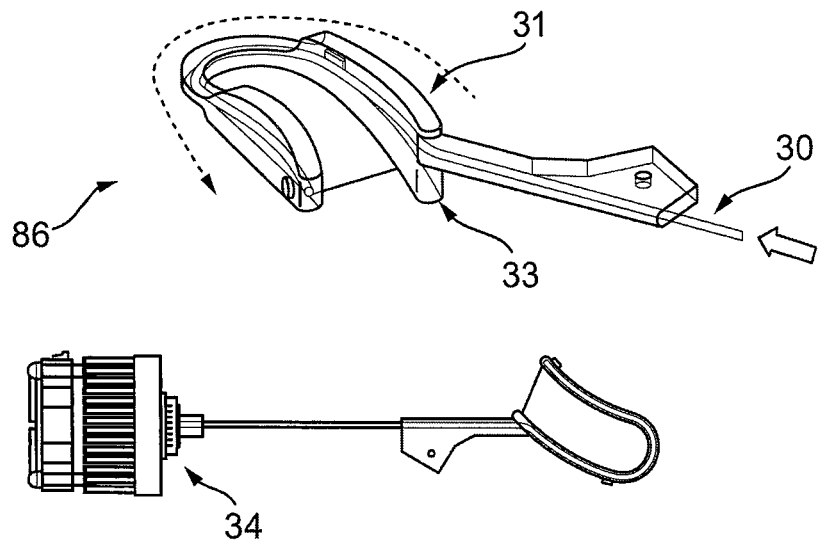
FIG. 28a shows the construction of the light pipe triple tray of FIG. 27.
Figure 28B:
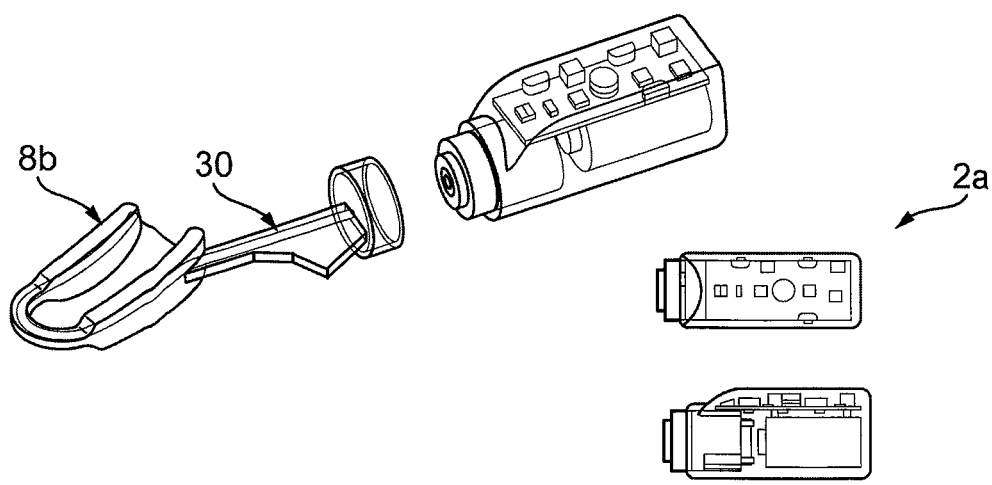
FIG. 28b shows the activation module of the light pipe including the LED light source, battery, activation circuit and coupling.
Figure 29:
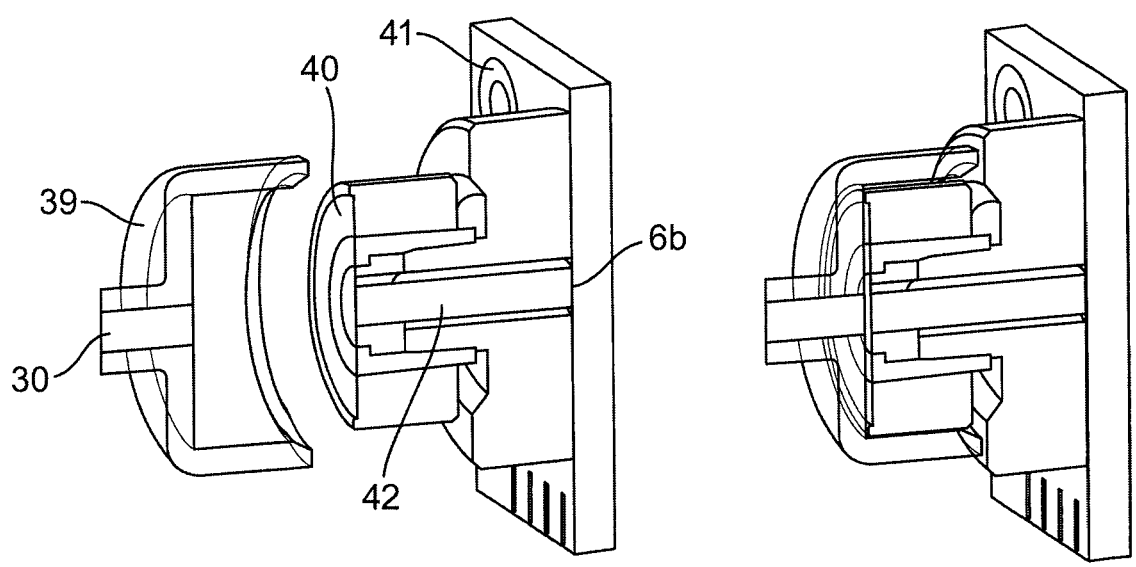
FIG. 29 is a cross sectional view of an embodiment.

In accordance with another embodiment, a dental illumination tray assembly may have optimized positioning of light sources: with light sources oriented toward the internal and external portion of the dental arch allowing the adequate curing of impression material 50 that would overflow outside the dental arch and the minimization of the total thickness of impression material distributed over the light sources and accordingly reducing the energy needed and the heat generated by the light sources in a patient's mouth. The tray 8 may not have a fillable palatal region. The palatal region is typically not necessary for the manufacturing of the dental prosthesis so removing the palatal region enables the saving of energy required and easing the overflow of material. The tray 8 may also have the configuration of a full arch, segmented, triple tray or single unit tray. The tray may have light traveling in the walls of the tray in order to reach deeper areas as shown in FIG. 21 and FIG. 22.

In embodiments, it is desired to amplify the light emitted. In the case of the light pipe configuration assembly, it is desirable to obtain the highest energy density at the entry point of the light carrying medium, e.g. light pipe or fiber optic, it is accordingly desirable to be able to augment the light density of the emitting surface of the light source—this is known to be difficult to achieve in optical designs. Since each light source has a maximum density at its maximum electrical rating, it may be desirable to use optical means to increase the light density. To increase light density, it was found that one could use a beam splitter with two source with narrow spectrums of wavelengths (like 390 nm+-20 nm and 480 nm+-20 nm) and combine these using a semi reflective mirror like a beam combiner. That then allows the addition of the two LEDs powers in a same cross section of 2×2 mm LED for example. This beam splitter-combiner may be placed at 45 degrees which would allow, for example, the short wavelength to pass thru and would reflect the longer one on its surface or inversely depending on the coating.

Another way to increase the light density entering in the lightpipe would be the use of a long tapered prism (not shown) that includes 2 LEDs at its entry (2×4 mm) and 2×2 mm at its exit. A laser light source is probably the most efficient coupling of light with the less losses at the light entry point. Placing the light pipe in almost direct contact with the emitting surface of the LED (minimize the distance) allows a very high coupling efficiency—it is important to keep the light pipe within a few hundred of microns from the surface of the led surface in order to maximize the coupling efficiency.

This embodiment may include a monitoring sensor (not shown) to determine if the coupling between the light pipe 30 and the light source is good before turning on the full power. Since all the light travels in the diameter of the fiber entry point the area may be precisely aligned and cleaned to avoid burning or melting of the plastic light pipe or bad coupling. An air gap may be included around the light pipe 30 to keep the light inside the light pipe 30. It is possible to make a light pipe using a plastic core with air as a cladding the difference in refraction indexes enables light to reflect inside the plastic. Furthermore, it may include features on the surface of the light pipe to enable light to exit from the tray along the length of the light pipe 30 as shown in FIG. 30. An LED light engine of the light pipe may be cooled by a heatsink 37 with phase change material for improving heat dissipation and reducing weight. Alternatively, the walls of the may be thermally coupled with the LEDs 6 in order to use the plastic of the tray as heat sink to prevent burning. A gel may also be used between the LEDs 6 and the walls around the LEDs 6.

In yet another embodiment, the assembly may have an over-tray attachable to it. The over-tray may have mechanical locking attachment features to allow the retention of the over-tray with the assembly. The assembly may have an attachable over-tray pre-filled with impression material. The prefilled over tray may have an assembly of different viscosity placed at different location in the tray as shown in FIG. 8. It may also be coated with chemical adhesive. It may be covered with an opaque lidstock to prevent the premature curing of the impression material. The lidstock may also be a co-injection molded cover that is bonded to the upper side walls of the tray and is configured so that the unattached area can be removed to expose the tray material. (In embodiments, the impression material may be very sticky in an uncured state in a pre-filled tray and the use of a separation agent between the lidstock and the impression material may be desirable. A non-polar lubricant was found useful to keep the lidstock easily removable from the impression material. Since the impression material is typically polar it has an affinity to other polar molecules and in the case of a polar lubricant will migrate inside the impression material volume overtime and reduce the effect of this lubricant. The use of a non-polar lubricant between the lidstock and the impression material provides a good separation mean while keeping a good adhesion to other layers of impression material even in the presence of small quantities of lubricant. Any suitable non-polar lubricant may be used, one example of a suitable non-polar lubricant is petroleum jelly. In embodiments, the non-polar lubricant could also be used to increase wettability (teeth surface-impression material) and decrease adhesion of the impression material with restorative present that may be chemically bonding to the impression material.

In yet another embodiment the assembly comprises an electronic monitoring system (not shown) that verifies if the tray meets the electrical and optical requirements in order to be used (not shown). The monitoring system attached may use a modulation of light to measure illumination. The assembly may further be verified by an independent assembly to determine if it works correctly. The monitoring assembly may have one or more LED light sources as a photo sensor to measure the light from other LEDs on the tray. The tray may be segmented into different sections for illumination control or monitoring purposes. The tray may be attached to a driving circuit to drive the different light sources at different powers or that monitors the value of current and voltage and compares it to an acceptable range in order to monitor the usability of the tray and/or the led temperature. The circuit may also enable or disable the usability of the tray or detect that the tray is securely attached by measuring the impedance and/or the capacity of the connection. The monitoring assembly could have any suitable function, such as checking the connection between the tray and the illumination engine, an indicating that the illumination engine is not suitable for a light curing cycle, indicating if the battery is too weak to properly illuminate, etc. The charge status of the battery may also be verified by the electronic system in order to make sure that there is enough energy to cure the tray material. This "Readiness" or "suitability" detection system verifies directly or indirectly: temperature of the LEDs and surrounding, the battery remaining power, the quality of the physical and optical connection, the performance of the LEDs, the performance of the attached light pipe. This detection system is able to then clearly communicate to user if the system is OK to be used. It's crucial that this tray system is able to perform when placed in patient's mouth—the placement of a non-suitable/non-ready tray assembly may result in undesirable/uncomfortable/dangerous situations (e.g. uncured impression material in mouth). Accordingly, the electronic system measures the above parameters using one or combination of the following items: thermocouple, ammeters, electrical resistance, quick discharge assembly with voltmeter, embedded electronic counters that counts the number of usage.

In yet another embodiment, the light sources may be accompanied with reflectors and diffusers to orient the light at the desired location and intensity as shown in FIG. 10.

The LEDs 6 may include some side-emitting and/or Bottom emitting LEDs. For example bottom illumination projects towards the buccal or lingual anatomy and the side emitting LED's emit perpendicular toward the vestibules as shown in FIG. 4.

In another embodiment, this assembly may be modular allowing the attachment or detachment of some illumination portions to fit different shape and size trays. (not shown)

Further a solid illumination and deformable (lightweight plastic) over-tray may be attached together and may not be detached from one another until the impression 50 is casted in order to minimize any distortion of the impression enabling very low cost disposable over-tray with minimum plastic secured from distortion by the attachment to a solid illumination tray.

In another embodiment, the assembly may comprise a power monitoring electronic system (not shown) with a means to detect the distance between sources (in the case of flexible illumination) or the degradation of light source and enables adjustment when necessary.

Light sources in an assembly may comprise at least one of these following ranges 300-500, 600-700 or 780 to 1000 nm. Blue light (465 nm) may be used because of its relatively good penetration (compared to UV) and because of the high energy it releases and because the photo initiators working with blue are well known and easily available. UV illumination in the range of 350-410 nm may enable the reduction of an air inhibited layer. The assembly may further include a temperature measurement means in order to avoid overheating and alert to turn off the illumination accordingly. The current consumption may be a good monitor of the temperature since LEDs 6 have a different consumption depending on the temperature. A thermocouple or other thermometer in chip may also be placed on or near the tray.

In yet another embodiment, the tray assembly may be used with bleaching gel for teeth bleaching. It may also be used for antimicrobial purposes with reactive gel. (for periodontal treatment).

In another embodiment, flexible retractable PCB strips 29 may be used as shown in FIGS. 23 through 26. The strip is a linear array of LEDs 6 attachable and detachable from the tray 8. This array of LEDs 6 allows illumination of the tray 8 and may be inserted into a tunnel or channel within the tray. As in other embodiments, reflector and optical channels may be created in order to bring light in all the areas of the tray. Further, this tunnel may protect the PCB from contaminants of the mouth and allow it to be reusable without sterilization. The strip 29 may have different flexibility in the length of the same flexible, retractable PCB strip since the first portion entering the tunnel will experience more curves while the terminal portion may be more rigid to provide the necessary force to counter act the friction of insertion. The flexibility of this retractable PCB could be obtained by using a flexible material, such as nitinol, attached to the PCB. In the case of a retractable PCB it may be desirable to increase the number of LEDs thereon in order to spread the heat power and distribute it more evenly across the PCB for better dissipation. This prevents excessive heating of the LEDs which could lead to premature degradation of the LED. Also, in order to remove this isolation created by the airgap between this retractable PCB and the walls of the tray, the channel may be filled where the retractable PCB fits with an optically clear, thermal coupling agent. For example, the channel could be pre-filled during manufacturing, with some Glycerine. The amount of glycerine may be calculated to accommodate this retractable PCB volume without spills of glycerine. With an assembly using such a retractable PCB, it is possible to obtain a smaller dimension in the retromolar bridge in the dual arch tray because of the smaller cross-section dimensions of this retractable PCB compared to the light pipe, approximate 2×2 mm for the light pipe and approximate X1 mm cross-section for a retractable PCB. The retractable PCB may also have a small enough thickness to be inserted in a triple tray retromolar area (around 2-4 mm). Since the LEDs 6 are all in a line, it may be easy to analyze each LED 6 precisely in order to ensure proper function prior to use. While being deployed in the tray the LEDs may also be verified and counted by a photo sensor.

In yet another embodiment, prefilled trays 1 may be achieved by pouring light curable impression material 50 directly into the light emitting tray in the case of a single use tray (or a tray insert in the case of a reusable light emitting tray). The material 50 is then encapsulated with a removable lidstock in order to prevent any leakage or displacement of the material from the tray. This assembly may then be placed in a container that blocks exciting wavelengths to enable a long shelf life. The prefilled tray has the advantage of removing the step of filling the tray and enabling adequate amount of material 50 needed to minimize the excess overflow material in the difficult to cure areas. In yet another embodiment, in order to prevent overflow of the heavy body impression material, a semi permeable, thin, translucent membrane may be placed on top of the heavy body material during manufacturing. This would allow the containment of the heavy body while keeping a good chemical bonding to the lower viscosity material over this membrane or mesh. Alternatively, this membrane could be made to chemically bond to the impression material. This semi permeable membrane described above membrane could also be made with an elastic material that concentrates the forces of the heavy body on the wash material to increase sulcus penetration (not shown). The light curable impression material may consists of a high viscosity (heavy body or putty like tray material) that allows good control of the material and can allow the creation of pressure over the uncured low viscosity wash material. The assembly encapsulation may be achieved by spraying the filled tray with a mixture of glass filler and initiator that would cure the top layer of the material. This thin crust can be then broken by clinician or by patients teeth. The encapsulation may consist of a plastic sheet that can be peeled off. Further the encapsulation may be created by using UV light for a predetermined time to create a crust. UV light has a lower penetration inside the resin and therefore allows more control of the thickness with a less sensitive timing. Encapsulation may also be achieved with an inert gas while curing with UV or Blue light in order to remove the oxygen and the inhibition layer created. On the edges of the tray, where the paste is exposed to air, a thin oxygen inhibited layer may form. However, the fast curing speed of the material will minimize the oxygen inhibited layer that may form on the surface.

Further, the body (high viscosity) material 17 may have reflective particles like titanium oxide. The reflective particles reduce light penetration, but increase the distribution of light inside the impression material due to light scattering. Accordingly, the particles enable the diffusion of light making the material cure in undercuts of the dental anatomy.

In another embodiment light curable wash material may be placed in the vicinity of the dental preparation margin or in the periodontal sulcus even with the presence of blood and saliva. A 250-700 micron I.D. needle may be used to deliver the wash material precisely in the sulcus. The material may be quickly cured just after placement in the sulcus and before the tissue recovers and closes the space. The wash material may be transparent or translucent to allow direct visual observation of the tissues thought the material during application in the gingival sulcus and on the margins of the tooth to be restored.

The wash material may also be cured (using an independent light source e.g. a normal curing light) before the placement of the body material and the light emitting tray over to capture the wash. Incremental placement of the material is possible as the oxygen inhibited layer allows the creation of bonds with subsequent layers. This pre-curing method allows the minimization of the amount of overflow since the low viscosity is displaced by the heavy body material and is pushed toward the areas less likely to be reached by the light curing light (not shown). Further, the material may not be too sensitive to contamination and may be hydrophilic and may be translucent for better light penetration.

A wash delivery kit comprising a wash (low viscosity) light curable impression material and a small diameter needle with a syringe capable of creating a high pressure to extrude the material through the small lumen of the needle may be achieved. The wash material may have fibers and particles to reduce the "collapsibility" of the impression material by the gingival tissue. The wash material may be scannable by optical scanners or by micro CT as it is radiopaque.

Further, particles may be added to the impression material for either optical or physical properties and may be selected to be non-absorbing in the curing light frequency to allow the preservation of effective curing light. e.g. blue non-fluorescent particles are desirable in the case of a blue light curing initiator system. Refraction index of particles similar to the base resin may be desirable to increase depth of cure. A certain amount of scattering particles like titanium oxide may be desirable to obtain a higher readability by decreasing the translucency.

In another embodiment, the light curable material may be useful to create a peripheral impression for partial dentures. The clinician places a certain amount of impression in the peripheral portion of the tray to prepare a border mold.

The making of an impression using this light curable hydrophilic wash material to first fill the sulcus and then, in the second stage, pick-up the cured wash material with the body of the impression material enables unlimited working time and incremental filling of the sulcus when necessary. Unlimited working time is possible if the operatory field is illuminated with a filtered light removing curing wavelengths (for example, utilizing the well known orange filters). Alternatively, one can have virtually unlimited working time if the operatory light used to illuminate the operatory field is oriented to illuminate indirectly, for example the light may be pointed toward the chin of the patient. In the case of an operatory light without curing wavelength filtering (e.g. the typical orange translucent filters), wash impression material with longer curing times could then be used. If such a longer working time wash material is used, the curing time would need to be adjusted for a longer period. In other words, since high intensity operatory lights used for field visibility produce a certain amount of curing light, these can cure the wash material too fast, it is possible to use a less reactive wash impression material.

A light curing impression tray may have sensors placed in the buccal and lingual sides of the reusable tray to indicate extent of cure. For example, a miniature speaker can be embedded on one side and a microphone in the other side of the tray. It is known that sound transmission is different before and after curing of the impression material, modulating the sound signal. This signal can be then electronically processed to indicate the extent of cure. Alternatively electrical resistance detectors can be also envisioned.

Operation of Embodiment (for a Reusable Light Emitting Tray)

The impression material 50, 16, 17, 18, 19 may be prefilled into a single use tray insert 1, 1a that fits neatly into the reusable light emitting impression tray 8. Each specific tray 8 may have a specific matching prefilled tray insert 1, 1a. In use, the practitioner will simply remove the prefilled tray insert from a light protective over package 51 (bag, pouch, wrap, tray, or the like, not shown). The user will then place the prefilled insert into the light emitting tray 8, attach an activation module 2 and remove a non-stick protective liner or lid 48 covering the impression material. The user will, insert the tray into the patient's mouth, position the tray and patient and activate the module 2, which will illuminate the LEDs 6, light pipe 30 (or other curing light source). The light cure impression material 50, 16, 17, 18, 19 may cure in less than 1 s.

Operation of Embodiment (for a Single Use Light Emitting Tray)

The impression material 50, 16, 17, 18, 19 may be prefilled into a single use light emitting impression tray 8b, 8c, 8e, 8f. In use, the practitioner will simply remove the prefilled tray from a light protective over package 51 (bag, pouch, wrap, tray, or the like, not shown) and attach an activation module 2. The user will then remove a non-stick protective liner or lid 48 covering the impression material. The user will, insert the tray into the patient's mouth, position the tray and patient and activate the module 2, which will illuminate the LEDs 6, light pipe 30 (or other curing light source) for the appropriate time. The light cure impression material 50, 16, 17, 18, 19 may cure in less than 1 s.

What has been described and illustrated herein are embodiments of the disclosure along with some of its variations. The terms, descriptions and figures used herein are set forth by way of illustration only and are not meant as limitations. Those skilled in the art will recognize that many variations are possible within the spirit and scope of the disclosure in which all terms are meant in their broadest, reasonable sense unless otherwise indicated. Thus, the present disclosure should not be limited by any of the above-described exemplary embodiments, but should be defined only in accordance with the following claims and their equivalents. The architecture of the present embodiments described herein is sufficiently flexible and configurable, such that it can be utilized and navigated in ways other than that shown in the drawings.

We claim:

1. A dental tray system comprising:
    a dental tray having a body having a channel for receiving a quantity of photocurable dental material, a light conductor, and a connector portion, and
    a light engine having at least one battery or an attachment to an external power source, at least one light source, an integrated circuit, and a connector portion, and
    a charging station,
    wherein the connector portion of the dental tray directly contacts the connector portion of the light engine such that the at least one light source is directly coupled with the light conductor such that the light conductor emits light throughout the dental tray thereby curing the photocurable dental material,
    wherein upon contact between a first contact portion of the dental tray and a second contact portion of the light engine an electrical connection is made such that the integrated circuit identifies a type of dental tray or the changing station,
    wherein upon identification of the type of dental tray, the integrated circuit activates the appropriate light source dependent on dental tray type, and
    wherein upon identification of the charging station, the integrated circuit applies the correct charging sequence.

2. The dental tray system according to claim 1, wherein the light engine has more than one light source.

3. The dental tray system according to claim 1, wherein the electrical connection is made by an electrical device on the dental tray that directly and intimately contacts another electrical device on the light engine.

4. The dental tray system according to claim 3, wherein the electrical device on the dental tray and the electrical device on the light engine are the same or different.

5. The dental tray system according to claim 1, wherein the type of dental tray is a single arch tray or a double arch tray.

6. The dental tray system according to claim 5, wherein the type of dental tray has a different number of electrical devices present if the type of dental tray is the single arch tray and the double arch tray have.

7. The dental tray system according to claim 6, wherein the integrated circuit of the light engine is capable of identifying the tray type of tray based upon the number or location or orientation of electrical devices that are contacted by the light engine.

8. The dental tray system according to claim 7, wherein the type of tray can be identified regardless of positioning.

9. The dental tray system according to claim 5, wherein the type of dental tray has a different number of optical ends of the light conductor exposed in the connector portion of the dental tray when the type of dental tray is the single arch tray or the dual arch tray.

10. The dental tray system according to claim 1, wherein the integrated circuit of the light engine is capable of identifying the charging station based upon the number or location or orientation of electrical devices that are contacted by the light engine.

11. The dental tray system according to claim 10, wherein the charging base can be identified regardless of positioning.

12. The dental tray system according to claim 1, wherein the cross sectional shape of the light conductor is substantially similar to the geometric shape of the at least one light source.

13. The dental tray system according to claim 1, wherein the integrated circuit of the light engine is capable of detecting at least one parameter of temperature, suitability of mechanical connection, suitability of optical connection, battery level, degradation of the light source, or combinations thereof.

14. The dental tray system according to claim 13, wherein if one parameter does not meet predetermined requirements, the light engine is capable of notifying a user that at least one parameter has not been met.

15. The dental tray system according to claim 1, wherein the dental tray is configured to place and bond preformed orthodontic wire and bracket assemblies onto teeth.

16. The dental tray system according to claim 1, wherein the dental tray is configured to place a photoactivated solution only a patient's teeth and then apply the appropriate wavelength to a location where the solution was placed.

17. The dental tray system according to claim 1, an external light source is tethered to the dental tray by a fiber optic cable.

18. The dental tray system according to claim 1, wherein an external battery source is tethered to the light source by an electrical cable.

19. A dental tray system comprising:
- a dental tray having a body having a channel for receiving a quantity of photocurable dental material, a light conductor, and a connector portion, and
- a light engine having at least one battery or an attachment to an external power source, at least one light source, an integrated circuit, and a connector portion, and
- a charging station,
- wherein the connector portion of the dental tray directly contacts the connector portion of the light engine such that the at least one light source is directly coupled with the light conductor such that the light conductor emits light throughout the dental tray thereby curing the photocurable dental material,
- wherein the integrated circuit of the light engine is capable of detecting at least one parameter of temperature, suitability of mechanical connection, type of tray or charging station suitability of optical connection, battery level, degradation of the light source, or combinations thereof, and
- wherein if at least one parameter does not meet predetermined requirement then the light engine is capable of notifying a user that such predetermined requirement was not met.

* * * * *